United States Patent
Rossouw et al.

(10) Patent No.: US 11,160,225 B2
(45) Date of Patent: Nov. 2, 2021

(54) METHODS AND COMPOSITIONS FOR SELECTING CORN PLANTS RESISTANT TO DIPLODIA EAR ROT

(71) Applicant: Monsanto Technology LLC, St. Louis, MO (US)

(72) Inventors: Johannes Daniel Rossouw, Trevos Park (SG); Heyder Diniz Silva, Minas Gerais (BR); Gilberto Pozar, Minas Gerais (BR); Michael Kerns, Ankeny, IA (US); Humberto Gutierrez, Ames, IA (US); Justino Mario, Uberlandia (BR)

(73) Assignee: Monsanto Technology LLC, St. Louis, MO (US)

(*) Notice: Subject to any disclaimer, the term of this patent is extended or adjusted under 35 U.S.C. 154(b) by 2 days.

(21) Appl. No.: 16/700,508

(22) Filed: Dec. 2, 2019

(65) Prior Publication Data

US 2020/0084987 A1 Mar. 19, 2020

Related U.S. Application Data

(62) Division of application No. 15/784,421, filed on Oct. 16, 2017, now Pat. No. 10,492,396, which is a division of application No. 14/800,072, filed on Jul. 15, 2015, now Pat. No. 9,788,505, which is a division of application No. 13/524,716, filed on Jun. 15, 2012, now Pat. No. 9,095,105, which is a division of application No. 12/277,817, filed on Nov. 25, 2008, now Pat. No. 8,222,481.

(60) Provisional application No. 60/990,413, filed on Nov. 27, 2007.

(51) Int. Cl.
| | |
|---|---|
| A01H 5/10 | (2018.01) |
| C12Q 1/68 | (2018.01) |
| C12N 15/82 | (2006.01) |
| A01H 1/04 | (2006.01) |
| C12Q 1/6895 | (2018.01) |

(52) U.S. Cl.
CPC .......... *A01H 5/10* (2013.01); *A01H 1/04* (2013.01); *C12N 15/8282* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS 10,492,396 B2 * 12/2019 Rossouw ........... C12N 15/8282
2007/0039065 A1 2/2007 Laurie

FOREIGN PATENT DOCUMENTS

WO 2009/029771 A2 3/2009

OTHER PUBLICATIONS

Agrama et al., "Mapping of QTL for Downy Mildew Resistance in Maize", Theoretical and Applied Genetics, 1999, pp. 519-523, vol. 99.
Ali et al., "Molecular Mapping of QTLs for Resistance to Gibberella Ear Rot, in Corn, Caused by Fusarium Graminearum", Genome, 2005, pp. 521-533, vol. 48.
Anderson, B. et al., "Evaluation of Methods for Identification of Corn Genotypes With Stalk Rot and Lodging Resistance", Plant Disease, 1994, p. 590-593, vol. 78, No. 6.
Asea et al., "Validation of Consensus Quantitative Trait Loci Associated with Resistance to Multiple Foliar Pathogens of Maize", Phytopathology, 2009, pp. 540-547, vol. 99 No. 5, The American Phytopathological Society.
Database GeneSeq (Online), Laurie C. C., Nov. 1, 2007, XP002520536, Retrieved from EBI, Database Accession No. AJF62030.
Database GeneSeq (Online), Laurie C. C., Nov. 1, 2007, XP002520537, Retrieved from EBI, Database Accession No. AJF62029.
Database GeneSeq (Online), Qi et al., Oct. 25, 2006, XP002520525, Retrieved from EBI, Database Accession No. DQ929634.
Dorrance, A.E. et al., "Diallel Analysis of Diplodia Ear Rot Resistance in Maize", Plant Disease, Jun. 1998, p. 699-703, vol. 82, No. 6.
George et al., "Identification of QTLs Conferring Resistance to Downy Mildews of Maize in Asia", Theoretical and Applied Genetics, 2003, pp. 544-551, vol. 107.
International Search Report for PCT/US2008/084652 dated Apr. 23, 2009.
Jampatong et al., "QTL Mapping for Downy Mildew (*Peronosclerospora sorghi*) Resistance in Maize", Proceeding of the Tenth Asian Regional Maize Workshop—Section III: Biotechnology Tools & Uses, 2008, pp. 291-298.
Martin et al., "Colocalization of QTL for Gibberella Ear Rot Resistance and Low Mycotoxin Contamination in Early European Maize", Crop Science, Sep.-Oct. 2011, pp. 1935-1945, vol. 51.

(Continued)

*Primary Examiner* — Medina A Ibrahim
(74) *Attorney, Agent, or Firm* — Thompson Coburn LLP; William A. Holtz; Lawrence M. Lavin, Jr.

(57) ABSTRACT

The present invention relates to the field of plant breeding and disease resistance. More specifically, the invention includes a method for breeding corn plants containing quantitative trait loci that are associated with diplodia ear rot (DER), a fungal disease associated with *Stenocarpella* spp. The invention further includes germplasm and the use of germplasm containing quantitative trait loci (QTL) conferring resistance for introgression into elite germplasm in a breeding program for resistance to DER.

9 Claims, 6 Drawing Sheets
Specification includes a Sequence Listing.

(56) References Cited

OTHER PUBLICATIONS

Nair et al., "Identification and Validation of QTLs Conferring Resistance to Sorghum Downy Mildew (*Peronosclerospora sorghi*) and Rajasthan Downy Mildew (*P. heteropogoni*) in Maize", Theoretical and Applied Genetics, 2005, pp. 1384-1392, vol. 110.

Olatinwo Rabiu et al., "Inheritance of Resistance to *Stenocarpella Macrospora* (Earle) Ear Rot of Maize in the Mid-Altitude Zone of Nigeria", European Journal of Plant Pathology, Sep. 1999, p. 535-543, vol. 105, No. 6.

Phumichai et al., "Detection and Integration of Gene Mapping of Downy Mildew Resistance in Maize Inbred Lines Through Linkage and Association", Euphytica, 2012, pp. 369-379, vol. 187.

Rossouw, J.D. et al., "Breeding for Resistance to Ear Rot of Maize, Caused by *Stenocarpella maydis* (Berk) Sutton. 1. Evaluation of Selection Criteria", South African Journal of Plant and Soil, 2002, p. 182-187, vol. 19, No. 4.

Rossouw, J.D. et al., "Breeding for Resistance to Ear Rot of Maize, Caused by *Stenocarpella maydis* (Berk) Sutton. 2. Inheritance of Resistance", South African Journal of Plant and Soil, 2002, p. 188-194, vol. 19, No. 4.

Sabry et al., "A Region of Maize Chromosome 2 Affects Response to Downy Mildew Pathogens", Theoretical and Applied Genetics, 2006, pp. 321-330, vol. 113.

Singh et al., "Graphical Genotyping of Genomic Resources (QTL-NILs and RILs) and Transciptome Profiling of Maize Genotypes in Response to Sorghum Downy Mildew (*Peronosclerospora sorghi*) in India", Proceeding of the Tenth Asian Regional Maize Workshop—Section III: Biotechnology Tools & Uses, 2008, pp. 220-223.

Van Rensberg, J.B.J. et al., "New Generation Maize Inbred Lines Resistant to Diplodia Ear Rot, Caused by *Stenocarpella maydis* (Berk) Sutton", South African Journal of Plant and Soil, 2003, p. 127-131, vol. 20, No. 3.

Van Rensberg, J.B.J. et al., "Resistance of Elite Maize Inbred Lines to Isolates of *Stenocarpella maydis* (Berk.) Sutton", South African Journal of Plant and Soil, 1997, p. 89-92, vol. 14, No. 2.

Wisser et al., "The Genetic Architecture of Disease Resistance in Maize: A Synthesis of Published Studies", Phytopathology, 2006, pp. 120-129, vol. 96 No. 2.

Xiang et al., "A Meta-Analysis of QTL Associated with Ear Rot Resistance in Maize", Maydica, 2010, pp. 281-290, vol. 55.

\* cited by examiner

| DER RESISTANCE LOCUS | Chrom | Pos (Left) | Left Flanking Marker | Pos (Right) | Right Flanking Marker | LOD | Additive Effect | Dominance Effect | Resistant Source | Resistance Allele (Left) | Resistance Allele (Right) | Geography* |
|---|---|---|---|---|---|---|---|---|---|---|---|---|
| 1 | 1 | 82.0 | NC0009449 | 95.7 | NC00025863 | 2.69 | -2.1 | -0.04 | CV174 | AA | AA | SA |
| 6 | 3 | 179.7 | NC0030587 | 204.2 | NC0019414 | 2.21 | 1.51 | 1.96 | CV183 | AA | AA | AR, SA, US |
| 9 | 4 | 95.1 | NC0032557 | 109.2 | NC0009620 | 2.44 | -1.85 | -1.31 | CV174 | CC | TT | SA |
| 14 | 6 | 38.4 | NC0003210 | 56.4 | NC0106527 | 3.19 | 6.86 | 1.77 | CV183 | CC | CC | AR |
| 14 | 6 | 38.4 | NC0003210 | 56.4 | NC0106527 | 2.10 | 3.99 | 2.62 | CV183 | CC | CC | US |
| 14 | 6 | 38.4 | NC0003210 | 56.4 | NC0106527 | 3.87 | 3.81 | 0.99 | CV183 | CC | CC | AR, SA, US |
| 21 | 8 | 78.9 | NC0082612 | 84.0 | NC0013946 | 2.63 | -2.09 | -1.11 | CV174 | AA | GG | SA |
| 24 | 10 | 105.5 | NC0009486 | 119.1 | NC0008643 | 2.99 | 4.23 | 3.18 | CV183 | TT | GG | AR |

FIGURE 1

| DER RESISTANCE LOCUS | Chrom | Pos (Left) | Left Flanking Marker | Pos (Right) | Right Flanking Marker | LOD | Additive Effect | Dominance Effect | $R^2$ | Resistant Source | Resistance Allele (Left) | Resistance Allele (Right) |
|---|---|---|---|---|---|---|---|---|---|---|---|---|
| 4 | 3 | 14.2 | NC0106389 | 88.0 | NC0009470 | 2.6 | -0.024 | 0.09 | 0.14 | CV162 | GG | GG |
| 12 | 5 | 79.0 | NC0111346 | 84.1 | NC0040366 | 3.88 | -0.03 | -0.01 | 0.1 | CV162 | AA | AA |
| 16 | 6 | 85.5 | NC0004030 | 99.0 | NC0088767 | 3.27 | -0.028 | 0.015 | 0.09 | CV162 | GG | CC |
| 20 | 7 | 64.5 | NC0040322 | 78.4 | NC0029362 | 4.02 | -4.69 | 24.56 | 0.14 | CV162 | AA | TT |

FIGURE 2

| DER RESISTANCE LOCUS | Chrom | Pos (Left) | Left Flanking Marker | Pos (Right) | Right Flanking Marker | LOD | Additive Effect | Dominance Effect | $R^2$ | Resistant Source | Resistance Allele (Left) | Resistance Allele (Right) |
|---|---|---|---|---|---|---|---|---|---|---|---|---|
| 8 | 4 | 71.0 | NC0201962 | 94.8 | NC0105550 | 3.7129 | 7.0521 | 0 | 0.0326 | CV162 | TT | ************ |
| 19 | 7 | 48.6 | NC0013158 | 78.4 | NC0029362 | 7.8693 | 11.1742 | 0 | 0.075 | CV162 | GG | TT |

FIGURE 3

| DER RESIST-ANCE LOCUS | Chrom | Pos (Left) | Left Flanking Marker | Pos (Right) | Right Flanking Marker | LOD | Additive Effect | Dominance Effect | $R^2$ | Resistant Source | Resistance Allele (Left) | Resistance Allele (Right) |
|---|---|---|---|---|---|---|---|---|---|---|---|---|
| 7 | 4 | 21.7 | NC0009057 | 46.8 | NC0199875 | 5.7692 | 7.4721 | 0 | 0.0498 | CV162 | TT | TT |

FIGURE 4

| Analysis | Chrom | DER RESISTANCE LOCUS | Position Left | Left flanking Marker | Res. Allele (Left) | Position Right | Right flanking Marker | Res. Allele (Right) | LOD | Effect Additive | Effect Dom | R2 | Donor |
|---|---|---|---|---|---|---|---|---|---|---|---|---|---|
| Across Locations | 2 | 1 | 36.5 | NC0202428 | AA | 55.4 | NC0201646 | TT | 2.91 | -1.51 | 0.0 | 0.07 | CV129 |
|  | 3 | 2 | 83.2 | NC0199309 | AA | 99.2 | NC0199941 | AA | 3.46 | 1.87 | 0.0 | 0.09 | CV162 |
|  | 5 | 3 | 90.7 | NC0110854 | AA | 107.6 | NC0202210 | TT | 4.60 | -1.81 | 0.0 | 0.10 | CV129 |
| Individual – Brasilia | 3 | 4 | 115.9 | NC0201774 | GG | 125.7 | NC0199741 | GG | 3.43 | 3.23 | 0.0 | 0.08 | CV162 |
| Individual – Pirasununga | 3 | 4 | 115.9 | NC0201774 | GG | 125.7 | NC0199741 | GG | 4.20 | 1.50 | 0.0 | 0.11 | CV162 |
| Individual – Uberlandia | 3 | 2 | 83.2 | NC0199309 | AA | 99.2 | NC0199941 | AA | 4.19 | 2.38 | 0.0 | 0.12 | CV162 |
| Individual – Brasilia | 5 | 3 | 90.7 | NC0110854 | AA | 107.6 | NC0202210 | TT | 5.59 | -3.96 | 0.0 | 0.13 | CV129 |

FIGURE 5

| DER RESISTANCE LOCUS | Chrom | Pos (Left) | Left Flanking Marker | Pos (Right) | Right Flanking Marker | LOD | Additive Effect | Dominance Effect | $R^2$ | Resistant Source | Resistance Allele (Left) | Resistance Allele (Right) | Geography |
|---|---|---|---|---|---|---|---|---|---|---|---|---|---|
| 3 | 1 | 221.1 | NC0015344 | 256.3 | NC0016137 | 3.14 | 0.47 | 2.14 | 0.12 | CV162 | GG | CC | Brazil (South) |
| 5 | 3 | 83.2 | NC0199309 | 99.2 | NC0199941 | -- | -- | -- | -- | CV162 | AA | AA | Brazil (Central) |
| 10 | 4 | 99.9 | NC0105197 | 120.8 | NC0200096 | 4.87 | -0.31 | 5.26 | 0.22 | CV129 | CC | GG | Brazil (Central) |
| 11 | 5 | 65.2 | NC0009668 | 81.3 | NC0200395 | 7.52 | -0.81 | 5.26 | 0.28 | CV129 | GG | GG | Brazil (Central) |
| 15 | 6 | 70.9 | NC0008833 | 88.0 | NC0201579 | 4.59 | 0.13 | 5.04 | 0.19 | CV162 | CC | AA | Brazil (Central) |
| 23 | 10 | 57.3 | NC0104512 | 71.7 | NC0201713 | 4.84 | -0.08 | 4.97 | 0.20 | CV129 | TT | CC | Brazil (Central) |

FIGURE 6

SEQUENCE LISTING

```
<160> NUMBER OF SEQ ID NOS: 79

<210> SEQ ID NO 1
<211> LENGTH: 500
<212> TYPE: DNA
<213> ORGANISM: Zea mays

<400> SEQUENCE: 1
aatccgcaac tgcaattttc tctgaatctg caatatagga atatatatat atatagtgtt    60
aggataaagc aagcttcatt ggcattaata ttaatgttgg gcaaaatcac ttagggcccg   120
ttcgtttgtg tccaggaatg gacacaggat tcgttccagc ttatcaaaac ttatataaat   180
tagagaaaca atccgactag gaatcgttac aggcctccaa tccgtgaaaa ccaaacaggg   240
ccttgtggaa tcaacactaa ctgaatttag aattagtacc tcaagctgtt catgaagccg   300
tttctggact tccatctgaa ggcgcagtgc ttcagtaaga tccatgctcc tatacaagaa   360
tgcccaatat catggaagag tattaaccaa gaagtaacag acaaagatga tcgtaaaatg   420
cactttaaca tataggaaaa ccttcaaatt agattttatg tttcaaaaga aacaacaaaa   480
gtgaatgcaa tggctcaatg                                              500
```

<210> SEQ ID NO 2
<211> LENGTH: 783
<212> TYPE: DNA
<213> ORGANISM: Zea mays

<400> SEQUENCE: 2

```
cccgggcccc tttaaattta acctgcagct gaaaaaattg acagagcatc atcatctgag    60
gtcagcaacc ctgatactag tacatcagaa acaggttctc cattctatca gcttagaaca   120
gatgctacaa aacttgttgc acaaacattt caaagagggc gaagaaatct ttggcagctg   180
gcaacaagtc gcttatctgt tctattatct agttcggctg tttgttcaac tagcacatac   240
caatttctga agaattatga agatcttgcc attttcattt tggctggcga agcattttgt   300
ggatttgaag ctagtgagtt ccgccagaag ttgaagactg tctgtttgaa ctacatggtg   360
tcctttcacc ggcaaaatgt atatgtatgt caatagctct gactcggttc ttaatgatca   420
gtgctcaaag ttcaaacatg tgaattttga actgctatca tcttttttaac tgcttaaaat   480
gtgtatgcag ttcatgacgt gtttgtagtc tttacgaaca ttcttcatat ttcttttctt   540
ttcttcattg gtagtgctgg tttcacagta gcccattttt gtaactgatt ttgatataag   600
ctaccagtgc ttttatgttt ctacaaaagg agtttgcagc tgatatgaac attagtcagt   660
gcagccacat tagaaggctt tgcattgata tgcaccataa ttccataagt cactaacatt   720
cacaatataa tctgtaagag aatacattaa taataatggt tgattgtacg tccctatcaa   780
aaa                                                                 783
```

<210> SEQ ID NO 3
<211> LENGTH: 661
<212> TYPE: DNA
<213> ORGANISM: Zea mays
<220> FEATURE:
<221> NAME/KEY: UNSURE
<222> LOCATION: (576)..(577)
<223> OTHER INFORMATION: n=a,t,c, or g
<220> FEATURE:
<221> NAME/KEY: unsure
<222> LOCATION: (1)..(661)
<223> OTHER INFORMATION: unsure at all n locations

<400> SEQUENCE: 3

```
aggaagcaga ggagctggag cctgacgctg ctctgcagct tgggccccat gaagtcggcg    60
gccaggagct ccacgagcgc catgtagtgg agcagccccg ccgaggccgc gttgagcagg   120
cccaccacga tgagcgccgt ggggctgttc tccctgtaca ccttggtgag cgccagcccc   180
agcgcgatcc cgaacggcgt cgtcgtggag aagaagaaca ccagccccgc cttcatcttc   240
gcgccgtact ccgcctgcag gatgcagccg ccgagtccca tgccctcgaa gagctggtgg   300
aagcacatcg ccgtcaccag cggccggatg gtgcacacgt tctgcgacgc tcccatgccc   360
agcccgatca ccaccgagtg cacgatgatg cccatctcca ggacctgcgc gtggactgtt   420
agctagtttc aatgcccatg agtcatgcat gaccgtacga actgcgatat gacacgcata   480
ttaccacatg gttttgctaa tatttattct gatttaggcc ccgtttcaat ctcacgggat   540
aaactttagc ttcctgctaa actttatcta tatganntga agtgctaaag tttagtttca   600
attaccacca ttagctctct tgtttagatt acaaatgggc taaaagtagc taaaaaaaag   660
c                                                                  661
```

<210> SEQ ID NO 4
<211> LENGTH: 942

```
<212> TYPE: DNA
<213> ORGANISM: Zea mays

<400> SEQUENCE: 4
agagcgatca cagggttcac atcaaaacac agatcccaat tatagaagga tgaataatga      60
attcacacaa tacatggagt ctatttacgt tccatgtctt agtttggcac tggatcccTT     120
aatggtgaac tataattaag taagatcttg gacagcttct tcacttcctg aacagatcta    180
ctaccaggta tgaggtatgg agcagatcgc gacaggttga acagacagtg gagctagtta    240
aataagcctg agatggcagc tccatgtata gttgcaggaa gctaagccta cttaattgga    300
ttcatagctg aggcaagctc gaaagatcga gctgagctga attggagtgc agtgggacca    360
aaactagaag ccaccgacgc tgcactggag ccaccgacac tgacagtgtc agcgcgcagc    420
ggaagcacac ggagcgggag catcatcaca gctcgccgag ctccgttgca tcagacgcaa    480
cggcgatcgg gcgggggatc taaccagctt cgaacttcgc gcgcaaacga gagaggcgta    540
gggagacgga cgaggagaag cgaagaagcc gaagtgccga acctgttgca gtcggtgcgg    600
agaggagcaa cgcggccgcg agcagcgcgg cggcacagca cgcgacggat ctgccgccca    660
ccgccattct tccttgccac ccgccgccta accgacacac gcggtctccc accgacagat    720
agatacagag ccgcgcccgc cctcccgtcc gtccgtctac ccgacgatct tgctccgtag    780
tgcggcgact acggttgcgg ccgaggggag gaatgggggg cggtggggag gagggcggag    840
atctggggag gtggggagtg ggacttaaag catgtgcggc aggcagcggc cgcgtctccc    900
tcccctcctc ttccccgtat tttactgcag gcatgcaaac tg                      942

<210> SEQ ID NO 5
<211> LENGTH: 771
<212> TYPE: DNA
<213> ORGANISM: Zea mays

<400> SEQUENCE: 5
gttctactgg tgttcaattg gtttctaaca tatgaaaaga tgtgccagcc aaaattctgt     60
tttgatctgt tagatgatgt atacatgccc atgtgatatt ggagttacat atggctaata    120
taaaaaggac acctgaacct taggcaagat gaaaggcagc tttcttcttg tttccattga    180
ttgttcctgt tttgactcat ttatgctgaa attgctgatg ctatttactt cttttctgac    240
cataaggatg ggggttgcaa cttctttgag tggtgcgatg ctccatctcc cgcccctgcc    300
aatgcacgaa ataacatggt tgtacactca gagacatcag caacagatat gctttgccca    360
tgcagtgctg gaacttgctt aattctcacc acaaagacag ggaaaaatgt tgggaggcag    420
ttctttTgct gcccattaaa tcaggtaaac tcaggattca ccaatgttac ctgaattcat    480
gacattttgc cgtaccagat agcggcctat actggtttgt tttctggaa gaacttggcc    540
cctttttatc tgacacaact tgtttaatta taacattgaa catctgcaac cctactcctt    600
cctgaatttg agtaatcaac atttgtggga ttttgaactt gtttaattat aacattgaac    660
atctgcaacc atcctccttc ctgaatttga gttatcaact aattgtgaga tttttattgc    720
aggatgccac ctatatcaat tgtattagat agaaattgcc gtaatgattt g              771

<210> SEQ ID NO 6
<211> LENGTH: 862
<212> TYPE: DNA
<213> ORGANISM: Zea mays
<220> FEATURE:
<221> NAME/KEY: UNSURE
<222> LOCATION: (779)..(779)
```

<223> OTHER INFORMATION: n= a,t,c, or g
<220> FEATURE:
<221> NAME/KEY: unsure
<222> LOCATION: (1)..(862)
<223> OTHER INFORMATION: unsure at all n locations

<400> SEQUENCE: 6

| | | |
|---|---|---|
| atcgagtatg ggcaaaggtg gtggtggatc ttgattacca tcggatgcaa tgagattgtc | 60 |
| aaactgattc gcttcttcac cgacaacatg gtcaccatca gtaacaggct cagtgttctg | 120 |
| caacaggtgc cccacttcac cttcagctgg cacccagga acctcgtttg actgtagagg | 180 |
| cgtcaggaat tcatctgtat cttcttttt atcgaggttg tcatagtctt cttcgtccca | 240 |
| atccgttggt aaggaagctt ccctggtagc accatcctct ttgtgggagt gataatcagg | 300 |
| gtaagattcc gtggcagcag tctctgtagg caagttttgc aattttcctg catagagcaa | 360 |
| agtgagcagg atagggaggc tttggttctt ggaaatggaa tgaaaatgta cgatgttttt | 420 |
| gctagggtta ggggaaaaaa agcaaagaaa gagaagagat gaataccagc tgcgtgggtg | 480 |
| ctactgcttc tgatagagac ggcagcaaag gtaatgccgg cgaggaagaa aaaggcagca | 540 |
| agtccaggtc caagaagccc tgaggaggag ctaccatatc aaaggtttag ctagctagaa | 600 |
| catgggaaag taagaggag aagaagatgg cggatggagt gagtctcacc tcctgctcgg | 660 |
| ccgaaccta gagtagattt gtcggcgccg tcatccgcgc tgtcggagtc ggaggaccag | 720 |
| ccagcgaagg agttggcggg gacgggccgg gagacgctct gacggggcgc aggcgcgggng | 780 |
| tcgagaggaa gaagagaccc gagccaggag tggagcaagg gacggccggc gaagatggtg | 840 |
| gagctggaga cagcatgcca tt | 862 |

<210> SEQ ID NO 7
<211> LENGTH: 580
<212> TYPE: DNA
<213> ORGANISM: Zea mays

<400> SEQUENCE: 7

| | | |
|---|---|---|
| cgactctaga ggatccccct ggtgcccgag agtactccct gaggcgattg cttttagatg | 60 |
| ttcctgacaa tgttgacatg gttatcttcc ccaattatgt gagttgcaga agtaacatgt | 120 |
| tgttgaata tggtaatgtg tttcacatct gattactgta ttttttttca ggagagcagc | 180 |
| attgaacgtg atgacattaa ggatcctttc actgaggtat aagagctact gttatctgta | 240 |
| acatatatgc aaaataaagg ggaaaatggc tctgtgtcct attgatgatc caccgactca | 300 |
| cttgggaaac aaaactggat agtctcactg tttagaaaaa aacactatag tttagcaaac | 360 |
| actgcacaga actactcatt attgcattgc agaaaatgat aggactggtc ggattatcgt | 420 |
| tggctgtatt tgataggttg catcatttat aaattctttt gtgcctgcag gtttccatgt | 480 |
| ttaagaaaaa ttatgaccat cttccaaagg atacatactt tggcctgtac aaagaagcaa | 540 |
| cacgtggtaa tccaaactac ttccttactt atggtaatgg | 580 |

<210> SEQ ID NO 8
<211> LENGTH: 359
<212> TYPE: DNA
<213> ORGANISM: Zea mays

<400> SEQUENCE: 8

| | | |
|---|---|---|
| tgatacacca aacatgtttc ccataaaattc taagtttaaa ttagatcatt caatcattca | 60 |
| tcagtataaa gaaatttggg tgagctttat gagacacagc atgaaatttg catttggtag | 120 |
| ttttatgcac caaggtgaag tgcagcataa gtatgaaaaa gcaccatatt tgatgtacag | 180 |

```
tatcaataat ttagggctgt gattaagcat attaggtggc agaacaagga aaacatcaca      240
tgttgatggc atattggaca atccttagta gtaagtagta acgaattact gagagtagga      300
agggaatata atgacgacaa acatttatgt agttggaact ccaaataagc accaacacc       359
```

<210> SEQ ID NO 9
<211> LENGTH: 420
<212> TYPE: DNA
<213> ORGANISM: Zea mays

<400> SEQUENCE: 9

```
cctgcaactg cttgggtatt gtacatctgt atgtgatgtg tcatgtgcac atgctttgcc       60
attttgcatt ggcaataata ggttgtgcat cccttcagcg ctacaaggag caaggatgtc      120
cgcttcagat taaatccgac tgtttagact gctgcaactg taatcataga gataaataca      180
ctatagaaac agtagtagga gccgatacga attaaaaaca acgaacaggc tgaaagatgc      240
agcgcttgtc tgcacaacat ccccaaagta tcttcgagtc gaatacaaca gggtaactga      300
gtgtaaccac agttcgtaca gaatttgtag agaaaatgaa ttgtccaaac caccggataa      360
attcatcttg ttacaatgtt tgctggcaga atagctcgca cagcacagga gatgagacca      420
```

<210> SEQ ID NO 10
<211> LENGTH: 538
<212> TYPE: DNA
<213> ORGANISM: Zea mays

<400> SEQUENCE: 10

```
ctctcatggc caatggactg ccagaggcat cggtggttgt tatgaccgcc atccttcctt       60
cattagagac atcataactt gctgaagaag atgcatcctc agcttccatc ataataaact      120
ttgcaatgtt cataactaac atgttctcaa aattgtcatc gtcccgctgc acatctttgt      180
aaccatatct aacgatgcaa cggtacatcc gatattcttt aggtccaatc ctacccacaa      240
ggtatcgctc gtccggtgaa acatacggca ctggcactga tttcacacaa aggaagacca      300
ggacttcatg gaaggcaggg agattagtga caaaatgtga gaaatggag ggtacaccag       360 tgaccagctc cgtgtaaatc aatccaatac caggaacccg aactatacca aggcttggac      420
cgagagataa gatggacctc attgatactt tgttctgtag gtcaaactgg tacttcctcc      480
ttaacccata gtgccaaatg tacatgactg acatgaatat gaaagcaagc acaagagg       538
```

<210> SEQ ID NO 11
<211> LENGTH: 739
<212> TYPE: DNA
<213> ORGANISM: Zea mays

<400> SEQUENCE: 11

```
ccccaccagg aatagttgcc tcggttctca gggcaacagt gtgcatgacc ttaacagctt       60
tcaagggaaa tctgtcgcaa aatcaaagtc ataagcttag cgccatgcat ctgtcgtgat      120
cttcaacata tatcacggaa gggaaacaca ccagaagact tgcaaatata tgcatacaac      180
ccaaaacaag gcaacagctt ttttaactaa aactacaaaa agtattaaca tatatgtttg      240
caacaatatc gttctagcag ctttattctt tgaataattg agccaaacca ggcaatccat      300
tgttagttag ttcgataaaa cttcaaagga aactgaaaga atacatgccg tatagatgtt      360
aggttcctga tttgatacac tgaaaatata gttaaacagt aaattccatt tccatagaag      420
gaaacataag gggcagcaat tccatccata acattatttt tcaggtatta attcatacgt      480
```

```
tacttatgat atatctggaa cttttgaaga atgcagtcac caaataacaa taatatagca    540
gtgcaaaagc atactaaaac aaacatagtg tccatggaac acaaaaaata tatatgatta    600
caatgtatat ataaatttaa tgtcatatct ggccatatag ttagggcagc tccaacaatg    660
acatttcagg tctcagctac ctcatagaga tccacctcag cattttttctt acgtggaaga   720 gagaaaagct accttttat                                                 739
```

<210> SEQ ID NO 12
<211> LENGTH: 740
<212> TYPE: DNA
<213> ORGANISM: Zea mays

<400> SEQUENCE: 12

```
atcagctcat gtatgcattc gatgtagttc cctgaggtaa atgaccacac cctgacagaa    60
tcttcactga cagacgccag atagttgccc gcggcatccc aacatactga ctgaataatc    120
tgtacgtggc cctacataaa aaacacaagc ccaaattaca gagtacatcg agaatagtgc   180
agagtaaatg caaaaaacat acagtgaagt tataacttag aatagccgct aagttgcata   240
cctacactta tcgcaattta ggaatgacat ggacatcaag gaactgatta taattcagga   300
aagaaacaaa atttcagcct ggatggtgat gagctgatca aatgctcatt ataccacaag   360
agttctcatc ataccacaat aaagtataaa catacactcg tctgtatgtt gtatctcaat   420
aatctagtac tccctccatt ccaaattata aaataatttt gcttttctag ttatattact   480
tttactatat atctagacat agtgcgtatc taaggggggtg ttttattgca ctagagcagt   540
agagctaata gttagttggc taaaaaatag ctagtggaat tagctagata acaaatatct   600
agctaactaa tagctaattt gctaaaatag ctcatagtta aactattagc tagactgttt   660
ggatatcttc agttaatttt agcagccaac tattagctct agtgcattca acatggtct    720 aagtacatag cacaagctat                                                740
```

<210> SEQ ID NO 13
<211> LENGTH: 434
<212> TYPE: DNA
<213> ORGANISM: Zea mays

<400> SEQUENCE: 13

```
gttcaggttt ttgtgaacaa caattcgaag ggctcctcag gatacagctc tttccaaact     60
ttttctgact caagtgtcga ctttgtttga gtggacgact caacgttgtt attgttcagt    120
attctgccat acactttctt gcagtcccctt atgtactgaa cctgaaagat atgtgctcga   180
ataatcaggt ccctcggttc tctgaatagc atcatcaaca agggtacatg catacaagat   240
gcttatagat catttccaaa tatagtcatc atatgtatca gtaaaaacca tgcagttggc   300
tgtctgattc agcgttgaga tcattcgtaa cacacccaag ggtacgtgaa ttacagatga   360
tcatggtggg tagggtgtgt accgggttaa ggcgatggca gtgccatatc cactcacaat   420
caagaggaac acgg                                                     434
```

<210> SEQ ID NO 14
<211> LENGTH: 418
<212> TYPE: DNA
<213> ORGANISM: Zea mays

<400> SEQUENCE: 14

```
tcttgtgaag aaaatatcgc aaagattccg atcatcttcg atactgatg tctctctata     60 aattggccag aatttcacca acaatttttg catctcataa ttgagagaga aacagggaga   120
```

```
acgttcagag acatggcatg gaaggtgggc actaggtgac agcgagcgct cgggatgaca      180
acgtgcgaga tccacagatg gagttgctag acgacggctc ggctatgaca ccatcgctat      240
cgaatgtcgt acaccttgcc accctagcac gacgccattg caggtctcac gcatgcatga      300
agggcaaggg attgagcatg ggatccacag gaggctatag aaattaccct ggctctgcca      360
aatgttcaat aaaaaatttc acaaagaaat agagtactag attgatgctc actatggg       418

<210> SEQ ID NO 15
<211> LENGTH: 418
<212> TYPE: DNA
<213> ORGANISM: Zea mays

<400> SEQUENCE: 15
tcttgtgaag aaaatatcgc aaagattccg atcatcttcg gatactgatg tctctctata       60
aattggccag aatttcacca acaattttg catctcataa ttgagagaga aacagggaga      120
acgttcagag acatggcatg gaaggtgggc actaggtgac agcgagcgct cgggatgaca      180
acgtgcgaga tccacagatg gagttgctag acgacggctc ggctatgaca ccatcgctat      240
cgaatgtcgt acaccttgcc accctagcac gacgccattg caggtctcac gcatgcatga      300
agggcaaggg attgagcatg ggatccacag gaggctatag aaattaccct ggctctgcca      360
aatgttcaat aaaaaatttc acaaagaaat agagtactag attgatgctc actatggg       418

<210> SEQ ID NO 16
<211> LENGTH: 574
<212> TYPE: DNA
<213> ORGANISM: Zea mays

<400> SEQUENCE: 16
attcgagctc ggtacccctg agcaagccct tgcccttgcc cttggccggc ccttgctgtg       60
ccccccggcc cttctctctc ctctccctca gtccctgtct tgtcctatcc tagtaaaaga      120
aaggacagtt tgattgcaca ggtagcccac cgctcaaatc atccgcttcc cctcgccctt      180
cctctctcac acccaaacaa acaagcctgc tggatcgacc gagttcagcc gagctagcta      240
cctaccttca gaaaccctcg caagctagca gcttctctca accctcgact tccttctacc      300
tatacaaccc taaatcagtt tgcttccttc ggttcttgcg aattgccagg aacgaaagag      360 cttttgccgct ctcgtgttac agaagactcg gaaagagaga tcgagaggaa ggagtaccag      420
atagacgtac cagcaggcag cagctagcta gagggggcgag cgagccatgt gcgactactt      480
cctacaaagg atggaggacg accgccacca ccaccatcag gccggaggag acctcacgga      540
cgtcgtccga ccggcggcg cgatgcatca ggca                                   574

<210> SEQ ID NO 17
<211> LENGTH: 1131
<212> TYPE: DNA
<213> ORGANISM: Zea mays

<400> SEQUENCE: 17
accctgtggt tgcatcagaa gaatcaactg tgcattcaac aaataagatc aatgactact       60
taggaacaat acctaatagt aaatttcgaa ttacgtaaca acaaggaac tttgaagctt      120 tcaggataac agatagagcg caaaaataaa tttcaccttc ctcaccctcc tccacttcct      180
ccactttgtt gtcccttcc aaaaactgga caacttcctc ctgctctggg ccatcacatt      240
tcacatccaa gaccacggct agatgataac acacaaccag catcaaacac tgtccccata      300
```

```
aaaattgaac agtagaacca aatcaatcta ggaagtgaaa tcctctgacc tttggttcc      360 tcttgctgca ccttctcctc ccctttggg tcatcacatt tcatccga gagagcagct       420 acatgataac gaaatcagca tcaaaaggct gtccacaaac aacaggatag tagaagcaag     480
tcgatctggg aaatgaaatc ctctcacctc tcggttcgtc ttgctgcccc ttctcctctt    540
ttgatgcgac cgccaccacc tcggcttcct gatccaaagc tctcgtcatc ttcgatgtct   600
tgtcctcgga tacatcttcg gcggggcggt cagcctccac tgcccccgcg ctttgcgag    660 aggccgccct cctccgggtg gctggggtcg gcgccacctc gcccgtccta cgaacggcag  720
tcctcctcgc tgttgcgcgc gcactggacg ccggaaccgg agtaggaaga ggcgcgggtg  780
tggcccgaat accgcggcga gtgctgcgca gcaccacgcc gggagtcttc acgttctcct  840
tcatctcgtc ctctcctcca acctccatcc ggatggcctc tggtgatttt accgatacgc 900
ggcggccgcg ggggagcggg ctaccgtgct gctgctcctc gacggccacc atcttcgccg  960
ccgacttcat cgccgacctt cctggcgtcg ccgtcggcag acagagagtc gtgccgatct 1020
cgtcgacccc gtcgacctga ccgacaagca aaaccccaaa tcaactacca ttccgaacct 1080
aataggactc acgaacatac tacacgagtg gaatcgagaa ctcaccgagg t           1131

<210> SEQ ID NO 18
<211> LENGTH: 527
<212> TYPE: DNA
<213> ORGANISM: Zea mays

<400> SEQUENCE: 18
tgtaaaataa agtaatttct gtggttgtaa attgtactac cttccttctc gattatctgt   60
cgcccgcccg ctagttcata tttgtcaatg ctgcctttgg cttgggcgga gggaggctcc  120
ccgcttcctg gtgtctgcag atgtaatcag ggtattgcct gatgctctct ggtatccgcc 180
gatgtgatca tgagcttatc aatcacctt tattttctga ttctgaaaac ttgagacttg  240
aagccgatat attattcagt agtcgttttg tctgtcgaat gtttatcagt ccctgcaagg  300
atcacaccac gctgcgctct ttgactgttt tggcttcggc ggagttgcgg ttcggttagt  360
cagtttgcat agttcctcgt tgcagatgat cgtagtttac aaaattctgg tcgtgttcgt 420
gttagttgtt gtgccgctct tgctcggttg atggcaagat ggcagctata tgtggaactg  480
aactgccctg tcaaatcaaa gccaaactga atcaccacca acaagca                527

<210> SEQ ID NO 19
<211> LENGTH: 341
<212> TYPE: DNA
<213> ORGANISM: Zea mays

<400> SEQUENCE: 19
ggcctcctgg agatctcttt gtttgcctcg atatagagga gccatcagat atcaagaggg   60
atggtataaa cttgtattca actgtgtcaa taagctatct tgaagctatt ttgggcacca  120
ttaagaaggt aagatatttc attatcagtt gtgatcttta attagtttca gtcgacgatc   180
actatcttgt tcagtaaaca gctagctttt cttcatacag cagaaaaata tctggtactt  240
atccacttca cttgataact ggagaacaga aacatgcaaa acttggtgtc cttataagaa  300
aaatagcctg gttactttat tccaatgttg atgcaatcag c                      341

<210> SEQ ID NO 20
<211> LENGTH: 554
<212> TYPE: DNA
<213> ORGANISM: Zea mays
```

<400> SEQUENCE: 20

```
ggctcggtcg tgtacgtcaa cttcggcagc atcacggtca tgacgcccgc tcagctcgcc    60
gagttcgcgt gggggctggc gaactgcggc aggccgttcc tgtgggtcat caggccggac   120
ctcgtcacgg gcgagaaggc tatgctgccg gaggagttct acgctgagac gagagagaga   180
gggctcttcc tcagctggtg cccgcaggaa caggtcctgt cgcatccgtc caccgggctg   240
ttcctgacgc actctgggtg gaactctacg ctggagagca tacgcgccgg cgtgccgatg   300
atctgctggc cgttcttcgc agagcagacg accaactgcc gatatgcctg cgcgaactgg   360
ggcattggac tggagatcga caacaatgtc acgagggacg aggtggcacg gctcatagaa   420
gaagccatgg acggcgagaa aggcaaagac atgaaggcga aggcaacagt gtggaaggag   480
aaggccgtgg cagcaacaga aagcggcggg acctcgagcg tcagcattga tcgtttggtc   540
gagttcctgc ttga                                                     554
```

<210> SEQ ID NO 21
<211> LENGTH: 384
<212> TYPE: DNA
<213> ORGANISM: Zea mays
<220> FEATURE:
<221> NAME/KEY: unsure
<222> LOCATION: (1)..(1)
<223> OTHER INFORMATION: n= a,t,c or g
<220> FEATURE:
<221> NAME/KEY: unsure
<222> LOCATION: (1)..(384)
<223> OTHER INFORMATION: unsure at all n locations

<400> SEQUENCE: 21

```
nctcccaact gacaccactc acttatgaga aaatgttggc caatcaagat attgcgtcgt    60
aactttgtac ttattcagga aatctattat tttgatgata attaaaagct ggcaagttag   120
aatgtaggtt gcaaacattt gcatgctttt gtttatcctg caatatctct ctattatgct   180
attttttctt ttggaaatca tagccagaga tttggagaaa tagcgttttg tgctatcaca   240
gctgatgagc aagttaaagg ctatggaaca agattaatga atcatttgaa acaacatgca   300
cgggatgctg atgggctcac acatttctta acctatgctg ataacaatgc tgttggctat   360
tttgtaaagc aggtatggct gcct                                          384
```

<210> SEQ ID NO 22
<211> LENGTH: 778
<212> TYPE: DNA
<213> ORGANISM: Zea mays

<400> SEQUENCE: 22

```
agctcggcac ccctggcagg ctgggagaca cacaccacca ctacactaac taaacactac    60
acaccagtac catttggtcc cggtttacaa aaaaaaaag aagcaccgtc ctaggttagc   120
acttgcgcta atcatgcact tcaacgcatc tcctttctca gaaagcaaac ctatctgttt   180
ctaaaaattg accagcagca cgtagtgact gagaaagata cttccgaatt aaggcatgtg   240
ggagctgcga taggttattt ctaacacatc tccttggttg tttagtgttt ttcttggttg   300
ataggaatct gcgttaagtg tgttcagcca tgtaataaca gaaactgaaa caaataaggt   360
aacagctttc gtacgacaaa gtcattgaaa tatatagtgt tgttctacaa gctctggtga   420
tggtgatgta tggcgatggc cacttaagt tcatgagaat gcatatgcta cagcctacag   480
ggcttaatta ctggctttaa ttagggcaat ttggtttggt gtatagctta tgttctgaca   540
```

```
gatgagcaat gcatgcattg tcagatgagg aggaataatt acattagttt gcagtaataa    600
acctgtaact atttccgtaa gggcttgttt gggtgctcta gtattcaacc caatacacat    660
ggattgagag aaattatggt gtaaattaaa catagcctaa atgtatcatg tatgtggttg    720
ttttacccat taaccgcaat cagcaacggc gtatcttctt cagcatcact atgccgca     778

<210> SEQ ID NO 23
<211> LENGTH: 529
<212> TYPE: DNA
<213> ORGANISM: Zea mays
<220> FEATURE:
<221> NAME/KEY: UNSURE
<222> LOCATION: (432)..(513)
<223> OTHER INFORMATION: n=a,t,c,or g
<220> FEATURE:
<221> NAME/KEY: unsure
<222> LOCATION: (515)..(526)
<223> OTHER INFORMATION: n= a,t,c,or g
<220> FEATURE:
<221> NAME/KEY: unsure
<222> LOCATION: (1)..(529)
<223> OTHER INFORMATION: unsure at all n locations

<400> SEQUENCE: 23
attagcaaca aaacaatcca gacacaaaat ggaagcgcag tcctccctct ccacctccac    60
cacagaaatg gaaattactt gccacctgct aaataactat agcaccccca ttaataacag   120
cagcagatgc agcggagtta cataatacaa gcaggcagac gacgagtgaa attaactccc   180
ccaccaaaaa ttcaaatcac acccaaccct tccaccgtga cgacaacaac acggcccca    240 gccaaacata cgacaaggga aaggaagaag aggggcaata ccaccaccgt gacgctgatc   300
cgcgtcggcg cagctcctga gcacctcccc gctcccacct ccggggccac caccgacgac   360
ggccccatcc accccctcca cagcagctgc cggcgccagg atcttcccga actccacctt   420
ggctggtaac annnnnnnnn nnnnnnnnnn nnnnnnnnnn nnnnnnnnnn nnnnnnnnnn   480
nnnnnnnnnn nnnnnnnnnn nnnnnnnnnn nnncnnnnnn nnnnnnctc              529

<210> SEQ ID NO 24
<211> LENGTH: 477
<212> TYPE: DNA
<213> ORGANISM: Zea mays

<400> SEQUENCE: 24
tgggcagggg tcaggtgcgt gaacggccaa gtgtccgccc tgtccttcca gaacctcagc    60
atagccaatc cagttccagt cccagctgct tccatatgca acctcaagaa cctgtcgtct   120
ctcgaccttt cctacaacaa actcaccggc cagttcccca cagcgctcta cagctgctcg   180
gctgctcggt tccttgacct ctccaacaat cgattctccg gtgccctccc agctgacatc   240
aacaggctgt cgtcggcgat ggagcacctc aacctgtcga gcaatggctt cacaggcagt   300
gtgccccggg cgattgccgc gttcacgaag ctgcggtccc tggttcttga caccaacagc   360
ttcgacggga cgtatccggg ctcggctatc gcaggcctca gcgagctcga gacgctaact   420
ctggcaaata ccccttcgt gccaggcccc atccccgacg acttcgggaa gctgacg      477

<210> SEQ ID NO 25
<211> LENGTH: 372
<212> TYPE: DNA
<213> ORGANISM: Zea mays

<400> SEQUENCE: 25
caaggaggag tacgacgctg aggtggagga cgacgatgca gacaacgtcg aggagtctga    60
```

```
cggcgacgac ttcgaccagg agaccggttg acccaggtgg ctcccccgtg cttcgtcggc    120
gtccttgagc gtcgtcatcc ccgctgtcca gtctgtattt cgcaatccct gagttgttcc    180
ttctatctag atacgctgtt accctattct gctgctgtct gttctcagga tctgagcatg    240
tccttgtcgt gtggaccttg tgtatgaaac aggtacatga ttaatcggtc caatttaaat    300
gctatattag tttcctctat ctgtgccaga tactgctact tcttaccatt tgttgtttg     360 tgtcatgacc ag                                                        372
```

<210> SEQ ID NO 26
<211> LENGTH: 475
<212> TYPE: DNA
<213> ORGANISM: Zea mays
<220> FEATURE:
<221> NAME/KEY: UNSURE
<222> LOCATION: (151)..(151)
<223> OTHER INFORMATION: n= a,t,c,or g
<220> FEATURE:
<221> NAME/KEY: UNSURE
<222> LOCATION: (429)..(435)
<223> OTHER INFORMATION: n= a,t,c, or g
<220> FEATURE:
<221> NAME/KEY: unsure
<222> LOCATION: (438)..(443)
<223> OTHER INFORMATION: n= a,t,c, or g
<220> FEATURE:
<221> NAME/KEY: unsure
<222> LOCATION: (1)..(475)
<223> OTHER INFORMATION: unsure at all n locations
<400> SEQUENCE: 26

```
atcttcggag tcgcttaggc cgagcgaccg aagcaggaac tcgacagcct ttcccttgtc     60
ccagtcgatc accgggcgaa cctctaaaac ctgcagcgta gcaaaagaat ttttttttc     120 gttgagtctt ggagcaagta tcaagatcaa nggcagtcgc agtagaacag tctaggctcc    180
taccattcgc ccgttggtta ctttgagacg agggaaggcc tccaagactt gtttcacgag    240
tcctgcgacc actttccagt cctgaaaaaa acaatagcat aaagctctca gtctcaggta    300
aattcgctac tgcttccctg taataggcgc ggtctgaatc tgatgcatcc tagtaaaaat    360
aaaaggatgt ctgaagccgt aatttcatcc atttctctac cgacaaaaaa aaggaaagat    420
aaacagatnn nnnnatnnn nnntgaaagt tcaggggca cgcaatctca ccttc          475
```

<210> SEQ ID NO 27
<211> LENGTH: 823
<212> TYPE: DNA
<213> ORGANISM: Zea mays
<400> SEQUENCE: 27

```
gggggggggg gatagaggtc cagtggcagt ggcaaggagg ctttggatgc tttagagtcc     60
acctgcccaa tgagaaaatg ctacgtcaat cggctgaaga tgaggccagt gacctcaaga    120
atcaaatatc acactggaaa aagctggagg tgttgttagc ttaaaacctt ttttgtctc     180 aaagtattgc ctcagtgtcc tgatagcaaa ggggcttccc tcgctcatct tgtaggctac    240
agctacagct gagataataa aactacagaa aatgctagat gctgaagcta gccagaaaga    300
gaaacttgaa gaagaaatag gtgttttgag aagccagtta ttgcagatga gtatggaagc    360
cgatgaggta attgttacta tcattgtcaa ggattttttc cccagggaag ctgctatatc    420
tttttgtaac ttatttctat ttctgacttg aacatgctgc cctaacatag tcggtatgtt    480
ttctcttcat tccatatttgg tcacatcaga caagaagtct tgataaagga gatgggccag    540
```

```
gaaaaatatt tcctggttta gattcattgg tgtctcagac tcgaggttca acccagag      600 agcaggacaa tggacagaag caaccgattg ccaaactctt tgaacaaggt atttgttatt   660 tattcttta cagtttctgc ttgatctgcc tatttcctgt aactctgtaa gaaatctcca   720
aaactaaaag taaactaatt gttgggctta acagttaatt atagcgattc acgaacccct   780
tagattacaa taaatggtgt gccaaaagat tcatgtgcta gca                     823

<210> SEQ ID NO 28
<211> LENGTH: 449
<212> TYPE: DNA
<213> ORGANISM: Zea mays

<400> SEQUENCE: 28
tgaagaacaa gaagtacttc tctgtagaaa ggattcagcg caaaaagaga gatatcacac    60
aacttctcag taaacataag catacagtta tggaagataa agtagaggtt gtaccaaaac   120
aaccaactgt tcttgatctc ttcaccaagt ctttacatga aaggatggc tgtgaagttc   180 taagcagaaa gctcttcaag ttcggcgata agagatact ggttaggatc cttgacagat   240
atcctttgca tttcccgccc ttgcttccac caggctaatc aagcttctct cttcttaagg   300
caatttctac caaggttcaa aataaaacag aagttcactt ggcaacaaac catacggacc   360
cacttattct tcactggtct ttggcaaaaa atgctggaga atggaaggta aaactccaaa   420
atgttttcca tttgttaaag ctgcaagca                                     449

<210> SEQ ID NO 29
<211> LENGTH: 253
<212> TYPE: DNA
<213> ORGANISM: Zea mays

<400> SEQUENCE: 29
caaggacact cccacgaagt gttctgatca tagggaccca agcggtgatg ataattactt    60
acctgctctt tgcattgggc cggctcgcca cactttacgt ctctgtcgcc ttactcggga   120
tatgttttgg tatctcgctc tccgtgataa tctcaacctc ctcagagctc ttcggactaa   180
agcactttgg aaagatattc aacttcatcg cattggcgaa tccggtaggc gcgttcctgt   240
ttaacaccct cgc                                                       253

<210> SEQ ID NO 30
<211> LENGTH: 731
<212> TYPE: DNA
<213> ORGANISM: Zea mays

<400> SEQUENCE: 30
tggagctcct actgaatctg aaacacttgt tgaagattcc acaaagcaga cagcagctgc    60
aaccacgttt gaacatggaa cggaatgcta cggttatcat gagaatggga gtttagttaa   120
tgaaatttct gcaccaaccc atttttcacc tgttggtgat ttgcagcata taggcaaaca   180
aatgaaagga agtgttagtg gcaaaatgga tatattgaag caagatgcta attccagcca   240
agatgttcat gttcctatga tccatgagat tatgatcact cctaacaaac gagcaattga   300
gaaagactct cgggttggtc aggcttcaaa aacaatttcg aagactgtca aggtgacttc   360
tagtaatgtt tctgatcaca catacgtttc caaggtattc acacattgat tttggacatc   420
ttcccatctt attcattgtt gcaatctgta tgtgcattct tttctaataa gttgactatc   480
gtcctggaca tggctcagca aagacagga aataaatgcc tcattatttt tgtgaaacgt    540
cataactaga attcataagc tatgccctat ctatttgaat taccttgatg catgccgaga   600
```

```
tggctagatt gatttcttca gtttcctgct actttagcca taggcatata ttatgtgttt    660
tattatgtag cccaaaacct gtacactttt cgtgaagcta taagctattt tttcatgaat    720 attttttaggg a                                                        731
```

<210> SEQ ID NO 31
<211> LENGTH: 608
<212> TYPE: DNA
<213> ORGANISM: Zea mays

<400> SEQUENCE: 31

```
tgtccgtcag ctccgccgcc tcatccagcg tcaggttgtg gttgcacccg gtgaaggcca     60
gcatgtcctt ctcgtatctg acgacgatca aggcaaacca atgcaagttc atccattgat    120
tgatctgcag ataatagccg gccaccgaac gctgtgaact ctcagctacc tcaggtgaag    180
cgcgatgtaa tgctgggact cgtttctcag ccgatcaacc agcgtgttgc cgagctcttc    240
gatctccttc ctgtactgga gcgcctcgta gttcgcgcgg caccgaagct tttgcagcga    300
aggagcgagg ccgttgttca cgatccgtga atccgtgtgt gtaaacctca ccactttgaa    360
cttcctcagg attttcgcaa agtctctgta gaaggaagcc tggaaaacgg agctggcgat    420
gcatcagcct attcagtacg tattcggtta tcctctaagc tgctgcaact gcaatgcaat    480
ccagtagagc aaacaagttg ttgactcgta ccctggacca ggaggtgggc gctctcacgt    540
acggtttcac ccttctgtaa tgtggtggga gggaatccac gatcacaatg tcttccttca    600
acgactcc                                                             608
```

<210> SEQ ID NO 32
<211> LENGTH: 901
<212> TYPE: DNA
<213> ORGANISM: Zea mays

<400> SEQUENCE: 32

```
tgatgaagca ccctccaatc catgaccaga cacctttca gctatctctc ttccttctgt      60
ttcaagtaca atcctgtgta atcattcaag aaaattaggt ataatgccac aaataattac    120
atactaatgt gggacgttat tcatctctaa gcttgagaat gatcctattg ctaaaccttt    180
gaatccagtg attaaaacca ttacaaaata gacgctcgga tattactcta ttgccatggc    240
ccccagttca aaaaaaaaac atgcggcaga tgacagtcag attatttcag agcaaaggaa    300
gaataataaa tgtacacaat aaagggaaca agaaaagaag ccctaatatc atgtatgtag    360
taagataagg atttacccctc catcaacaat ttcatcaagg cacaatagga tcatatccaa    420
attctcgagt gctgtccttt tgtcaaccat gtttctgaaa ccaccaagat tggaaacaca    480
ttcatataca atcagcatta acacaacaac atgtaacaga acaaaacagt ggttgcaaag    540
ataaagttta atagagggaa ataacttgaa gaagtcgttc gacagcatca gagaatccct    600
gaagaactga tgctaaaata agctcattct cttcttctcc tccagtaaca aaaaagtgca    660
ggtcttggat gaacttgtat accacaattt gaccgtcaaa cattacaatc tcaactgtta    720
aagagaaaca aagaaaaata tgaaatactt gaagagaaga acaaaaactc aaacagtcat    780
atctgcatgt ttaaggagaa atcaaggtca gtcagaagga aaactagccc aggctcattt    840
acagatttgt ggcatgagtg ggagctcgta caaacagtgt tatgactgag gttagtagag    900
c                                                                    901
```

<210> SEQ ID NO 33

```
<211> LENGTH: 490
<212> TYPE: DNA
<213> ORGANISM: Zea mays

<400> SEQUENCE: 33
ttcaattagc ttctgagcct tcgcaacata tctttccaaa gtggttagta gttttttcca       60
attcttgttc attacaaact catcacaata acgtatcata gcttcattgt cctaaataag      120
ggaacaattg gataaataag aatcaagaca attggagcga gggtggtcta tgtcttagtg      180
tagctaaaac tcaagagttt cgaatgtgtg gacttatcat gagctgaaat attagcattt      240
cacgtttatc tataagtaag catatcattt tttatttatt agagaatcag ccaagaagat      300
atagcttcaa ataaacagta atcttggtca aagaagttta gtgtaggatc acaatatgag      360
aacaaagcag tagacacacc tttgcagaaa aacttcgaga aaaaagatcc ttgaactcca      420
tataaagagg aaaacatatc gatcgagcat ctgtaggctt aaatcccccca aggagatcag      480
aaatgtcact                                                             490

<210> SEQ ID NO 34
<211> LENGTH: 1043
<212> TYPE: DNA
<213> ORGANISM: Zea mays
<220> FEATURE:
<221> NAME/KEY: unsure
<222> LOCATION: (999)..(1035)
<223> OTHER INFORMATION: n= a,t,c, or g
<220> FEATURE:
<221> NAME/KEY: unsure
<222> LOCATION: (1)..(1043)
<223> OTHER INFORMATION: unsure at all n locations

<400> SEQUENCE: 34
tcttttataa tacacagggt taatatcttt ggactttaaa aaattgaaac cagcaagaac       60
cttgtctctg aatatcaata tctcaatatt tatcatctca atgtccaaat gctgatttca      120
acatccttcc tgcagagctg tttgttttgc agtagtagcc atacttgttg cattggtggc      180
atctagtcca acgaaaggct ggagtggccg cagtttgagt ctacttgacc cgtaagttct      240
tctagaataa aaatacattt tattttgctg atcatgcatg gctgacctga cttgggaact      300
aataaacatg aaataacact taatgatgac ttggctgtta ttaggtttta gtgtatctga      360
cgaaatgatc ttgacatttg atgcttagga tcttagacaa atataagtgt acatcaccaa      420
attcaccatt gcaacgtctt atttaccttt ctggtgttgc tttgcatgtg gcgtcctgtt      480
tcagcgtgtt tgttctgctt ttctcatatt aatcgctgca acttcaatct tgttttctga      540
cagaacttat gcaagcaagt acatccccat cattgctagt gtcagtgaac accaacctcc      600
tacctggccc tcgtattta tggacattaa tgtgttggcc ttcctgattc ctgctgggat       660
tattgtaaga attatacttt gttaattcaa actgtaccgg caatactctt agttctgatt      720
aatcgatttt tacatgattc acagtcatgc ttccttgcctc tttctgatgc aagctccttc      780
atggtcttgt acttagtcac tgcagtgtat ttttctggag taatggtaag aatccttgcg      840
gtaggaagaa tctcttgcac tttttttat tatttacttg ttataacttt ctgtggcatc       900
catgctttgc taggtacggc ttatgcttgt ccttgctcct gctgcgtgta ttttatctgg      960
gattgctcta tctgaagttt tcagtgtgct cacacgatnn nnnnnnnnnn nnnnnnnnnn     1020
nnnnnnnnnn nnnnnaaaaa aaa                                            1043

<210> SEQ ID NO 35
<211> LENGTH: 377
```

```
<212> TYPE: DNA
<213> ORGANISM: Zea mays

<400> SEQUENCE: 35
tcatgcataa gaatcatcag tgtgttgatt aggatgcgcg tgaggcacca tctgagagag      60
cagttgctgc tgcaacaata gcttttgttg ctgctccagt tgctgttgca gttgttgttg     120
ctgctgctgc agttgctgct gctgctgctg ctgcttgagc aataacatct tgtccaacat     180
agagagtgga ggctgaggtg taaaaggtgt ctgagactgc aactgtagtt gtgacaaaag     240
atattgctgc tgaagcatat ttaacatttg cggatcttga gatatctcgg caagcttctc     300
aggtggcaac tgagccaaag ctggtcggtt ttgtggcatt aagttgtgtt gttgaaatcc     360
aataccaatg ttctggg                                                    377

<210> SEQ ID NO 36
<211> LENGTH: 774
<212> TYPE: DNA
<213> ORGANISM: Zea mays

<400> SEQUENCE: 36
aataaaataa aatgtgaatg ttgctcctaa ctgctgaact tggtaaataa agggagacag      60
catgctatgc tacatgttgt caatgttaca aacttctaaa aaatattta gtgctgaaag      120
aaaggtttgt atatattgac tgatctaact aggcagaaga tggtgtgtat gtgccacttt     180
cagcaaatta gttccagtat ctccatgtta tattgttaga aacagaagtt cgacatgaat     240
ccctaaacta cttcagaaac ctgagttggg aaaggaccaa gatacgggtg tatgatttca     300
actatttaac tgctgcttag cttttcatcag aaaacttgga tggaactggt caacaacaat     360
tgtgcctgta tgccgtgtat gtcatgaatt acctggtacg gttgaattgt ggaagctcat     420
cagatttac tgatcagata gttttgcatc agtttgaact ggggtgtaga gaaagaaggt     480
agagttgcag caagtatgtt tttatgtttc tgcaatgaca aatggaagaa caagtaacaa     540
aaggacatga aaatacatgc tgagcccagt aaacacaggc tagcaggtta ttaatttatc     600
atatgacatg ctctccaccc tgacaccagc aaattggcaa atgttgattg tttatctatg     660
gatcgtgcag agcagcaagg gacagctctg aaccagttt ctatatattg aaggaccta     720
aacaccagct ctgaaccagt tttctgtaga agatacatat aaatcaagaa caaa           774

<210> SEQ ID NO 37
<211> LENGTH: 703
<212> TYPE: DNA
<213> ORGANISM: Zea mays

<400> SEQUENCE: 37
gctagacagc aagggtctgg ccatactgtc cttgagccat gcgctgttgc acctgaaaga      60
agatcatctg gagcagggaa tattgctcga attcctcatc ccaccagcag cggggaaaaa     120
ctttcggata aaagtagctc ctcaccaaga agcatggcaa agaaggtctg gtagtcatct     180
gtaccctcct ttgaactgta cccctttaggc ctcatgtact tctctttgtt tctcagacag     240
tcttctattt gccttacgct gccaaattaa cttttggaca tgaaactagg caattttaat     300
gacaaatttt gtactgtgtg gatttgcaga gtccatcatt cacacccagg aagcctctcc     360
aatctgacaa cacttctcac agtcaagatg atgactcata ttctgtcact tcttcgtatc     420
ctttttttctt tcaaacatg gatcacattg aattctcatg tgaatcttat tgttctgtct     480
gtttagtgtc tccttttat ttagtttttt atgcatatga actccataaa attttggatg     540
```

| | |
|---|---:|
| gccactttt tataccttta taactgactt agtaaaaaag tttgcttcat ttgtattccc | 600 |
| caatttcctg agctgcgtac agaactgtaa cttcagcaag agctgggaaa actaagaaga | 660 |
| caactgttgc tgttgcacca acattcgtct gtgctaatcg tgc | 703 |

<210> SEQ ID NO 38
<211> LENGTH: 555
<212> TYPE: DNA
<213> ORGANISM: Zea mays

<400> SEQUENCE: 38

| | |
|---|---:|
| aatatagttt tcaaagaaag ctgttgtttc ccgtactgat atggcagttg tggtttgtgt | 60 |
| tgatcatgtt cagatttcca aattccattg gctgttgacc ctcccaaagc tggaagtagg | 120 |
| gaaaaaagga gttcaagggc atctattgct ttaggaattg gaattcctat tgtagcaata | 180 |
| ttcactgctc tgattctcgg catttattgt attaagaagc agagaaagag ttcgatgcat | 240 |
| gaaggtacca tcgttatttt tctcatttca attattttgt tatttaataa actggtaact | 300 |
| ctctttcagt ttttggttaa atccacatgc tatagcaaac ctactgagct gcactaggaa | 360 |
| ttgcaaaata ccttggatcc caaataaaca gagattcata aattttttt gaaagaaatg | 420 |
| gcaggagctc tgcctaatca ttaaaataag agagttcaga aaacacaatg tacaggtccg | 480 |
| aggaccgaga caagacagac tagcaaacac agcgtgagga acggtcccaa cagacccgca | 540 |
| caaaacagct aaacc | 555 |

<210> SEQ ID NO 39
<211> LENGTH: 1310
<212> TYPE: DNA
<213> ORGANISM: Zea mays

<400> SEQUENCE: 39

| | |
|---|---:|
| cagtcttgca tgcctgcagg attaaatcac tatggagcaa attaggctgt ctccaacagt | 60 |
| gccggtaaaa tgtcctctac cctaaatata tcatacatat gtgtcttgta aggctaactg | 120 |
| caacggtgcc cccttggaac ccctccccctt gcatgccggc tgtaggggac actctacggc | 180 |
| cgcagcggtg cccccctacag cgcccccccta cgcgtcggac cccttctctc cccccccagat | 240 |
| atagtgtgtc actattcatc cctctaaaca ctgtgctgtg ggtacacgag taattgttag | 300 |
| tagataaaaa attgatagtt gatatagaaa atgatatttt atagttgtag tggggtatag | 360 |
| ggggaatatt taggggaacc gctgcgggag atgaaaaaat agggggaaaa ataggggaa | 420 |
| aaagtgatat aggaaaaaaa aattagggat aacggttgcg gatagcctaa gcgtccagca | 480 |
| acaaacccta atcatccgc tataatatag cggctctctc tctccctcta ttattggcgg | 540 |
| acacacgacg ctcgctatgc actgttcaat cacgcacacc aactccttcc attctctctt | 600 |
| gcgcttgctc gtcgtcgtcg tcgaagtcgt tggagctctc gacgatgctg agctcgacgg | 660 |
| cctcgccgcc ttccccgtcc ctgtcccac ccatggagca aagatgtcg aaccatcgcc | 720 |
| aagctacacg tccgagccat gggtagtaca acgcatgcgg cgtggtcgag agggagtaga | 780 |
| cgagggacgg cggaggtcg gcggctgggg acgacgttgg caaggtggac cacatgatgc | 840 |
| ttgtcgccaa tggctacacc gagctactag tgttcctcaa ctacctcagc gtggaaaacg | 900 |
| cggacgcctg gctggtgctc aaggaaatgt tgagcacta tagtctatag acatgaacga | 960 |
| tgtaatgcat ttttttaaaa gaagtcggat aaccttttcc ttatagaaac acgagtagta | 1020 |
| atgtaggata caaaatgtaa ttattttaat tagttcctaa ttcatttttg ctagaaatga | 1080 |
| tttttattgc gaaatctggc acactgtaga tatagaggac tgaatttagg taacattgct | 1140 |

| | |
|---|---:|
| ggagatgacg aaaatataga tgacagaatc tttaagagtg tgttgtaaag gataaagaat | 1200 |
| attcttatag agggtgaatt tttatagagg gtgaatttta gaggacgttg ctgaagacag | 1260 |
| cattagagaa cagtactgca gatgggtggg cggggagag agaacttgat | 1310 |

<210> SEQ ID NO 40
<211> LENGTH: 570
<212> TYPE: DNA
<213> ORGANISM: Zea mays

<400> SEQUENCE: 40

| | |
|---|---:|
| tgctcgtggt cccaggcggc gtggccgacg tagaacctca ggtcctgggt cctgatcgcg | 60 |
| ccgctgttca tcagggcggc ggccttctcg aggtccgtcc ggaagccgta gcagatgcct | 120 |
| ggcaccacct cctcgaaccc cttgaggcgc gcgctgtcct cggtcctcac caggaacatg | 180 |
| ctcatgtcga cggggcctcc gaagaagagg ggggagtcgc cgaagggcgt cgcctggtct | 240 |
| cggaacatcg ggttcacgtg cttgatcttt gtgtagagcg gacggttcat gatgactccg | 300 |
| aacgggccgt cgaacgtgcc ccttgtaccg agcctgagga ggaagatgac ggttctttcg | 360 |
| aagatgctgt cgtcgtctag cgcttcggta gcaaccagaa cgcatcctgc ctctggcatc | 420 |
| gtaatagcat gagcccactt tgagggagc tgtaatggat ctcctgagga cgccttcgac | 480 |
| tctgatggag tacttggatc cactaatagc tcctgattca gagacagaag cagatatgaa | 540 |
| aaaccccaag gtatatggct gcgctcacca | 570 |

<210> SEQ ID NO 41
<211> LENGTH: 730
<212> TYPE: DNA
<213> ORGANISM: Zea mays

<400> SEQUENCE: 41

| | |
|---|---:|
| ctctctttcc cgtttcctac gctgcaacca aaatattgtg tctccaaaca ggtattgggt | 60 |
| tgaattgatg taaatatac tatagtagta tcatggcatt cggaaaactg tgatattata | 120 |
| aaccgtggtt ttaaaaaaac agtgttctca aacaggccct gggatgtatc atagagatat | 180 |
| gctatgcgca ggctttcttt tgtattagtt gatagatatt actttgagga gagatcctct | 240 |
| gtttcacttg tttatttct taaactgttt cacctttaa gatctatggt catgggtcat | 300 |
| ggcgcaccat actcatagag cttatgtgga attattatgg ccaaaaaata taaaaagat | 360 |
| ggaatttgtg acataggatt gattaagagt gcaaatacta tgtctgttta ttaattgcct | 420 |
| gaatgtgtat gaaccatggg attttatgg agttctgact cgattccttg tgtttaatgt | 480 |
| taggtaccct aatgacagtt ttgatcgcta ttggcagcca tttccagacg acaagcatgc | 540 |
| tgtcagtagc acccaaaatg ttacatcagc cgacttctgg aatcttcccc ctcctgatgt | 600 |
| gtttaacaca gctttcatac cacaacaaga tgcaccggtt gtgttacaat ggccttcaat | 660 |
| gcctctccaa aattatagct attatgttgc cctttacttt tgtgatacat tgctgataat | 720 |
| taaagacctt | 730 |

<210> SEQ ID NO 42
<211> LENGTH: 676
<212> TYPE: DNA
<213> ORGANISM: Zea mays

<400> SEQUENCE: 42

| | |
|---|---:|
| cgctgtgaca atgaaccagc tccttggacc aggttggaca aaacacttca tgtcatcact | 60 |

```
gtcactgcta gattagttct tgaccttaga gaaaaaaaat gtgtgatctt cctgctgaca      120
tctgtactct gcttttagc gacgatcacg gtgaccgtcc aagaccattg ccaaagataa       180
aggagctgca aggtgcaact gatataacag agaggaaagg gcgcccttca tgggattatg      240
atgtatgtac atctgtttct tctttcagtt ttaccataat atgttatgga atatggatga      300
gttgtattca ttgtgatagg ataaagatgg ctggaaatgg gtggtgcctc cgccagtcag      360
caggaagcct gttctatctg gggatcctga gaccgacaag caaatccgta gagcaacaaa      420
gcgtgttcat ttgtctgttg ctgaaaggct gcttaaaggt tcatgctctt ccgatttgat      480
ttattattta actcttgggt tcattttatg atattttgt gaaagcatgg tgttccctgt       540
tcctgcagaa tttgcttgtt cgatatgccg ggcggtgatt aaagaaccac ttacgactcc      600
atgtgcccac aacttttgca agacttgttt gcttggggca tatgatagcc agtcttctgt      660
aagggaaaga agctgt                                                      676

<210> SEQ ID NO 43
<211> LENGTH: 1012
<212> TYPE: DNA
<213> ORGANISM: Zea mays

<400> SEQUENCE: 43
gtcgacctgc agagcgtgcc ggggctggtg atcctgtacg gcagcatcgt gaagaagaag       60
tgggccgtga actcggcgtt catggcgctg tacgcgttcg ccgccgtgtg gctgtgctgg      120
gtcatgtggg gctaccagat gtccttcggc cagaagctgc tcccttttctg gggcaaggcc     180 ggccacacgc tcggccaggg cttcctcctc agccaggcgg ggctcccggc gaccacgcac      240
ttcttccacg gcagcggcgt cgtggagacg ggcgagatca cgcccttgta tcccatggcg      300
tccatggtct acttccagtg cgtgttcgcc gccatcacgc tcatcctgct cgccggctcc      360
ctgctcggcc gcatgaactt caaggcgtgg atgctcttcg tcccgctctg gctcaccttc      420
tcctacacca tcggcgcctt ctccatctgg ggcgggggct tcctcttcca ctggggcgtc      480
atcgactact ccggcggcta cgtcatccac ctctcctcgg gcgtcgcggg cttcaccgcc      540
gcctactggg tcgggcccag gctcaccaag gacaggggaga ggttcccgcc aaacaacgtc    600
ctgctcatgc tcaccggcgc cggcatcctg tggatgggct gggccggctt caacggcgga     660 gaccccctacg ccgccaacat cgactcctcc atcgccgtgg tcaacaccaa catctgcgcc    720
gccaccagcc tcctcgtctg gacctgcctc gacgtcatct tcttcaagaa gccctccgtc    780
atcggcgccg tccagggcat gatcacgggt ctcgtctgca tcactcccgg cgcaggtaca    840
gtacatatac acgattctgt ctacaatcac tactctactc tactactgcc agtgccagcc    900
tgatgatggt tcttgtaggc ctggtccagg gctgggcggc gatcgtgatg gcatgctct     960 cgggcagcat cccgtggtgc acgatgatgg tggtgcacaa gcgctcccgc ct           1012

<210> SEQ ID NO 44
<211> LENGTH: 330
<212> TYPE: DNA
<213> ORGANISM: Zea mays

<400> SEQUENCE: 44
ttacaagtca tttcaacttt tcgaatataa tttctcgtaa gatggatttt gttttctcga       60
tttgtaagat ggcttgaaag gacgtggatt ccttcgtagt tggacacaac gtggactcct      120
ttctgttgga tatgaatgtt aatccatcag caggtctgtc tagtgctaat cctaatctcc       180
ttggaattac aattaatatt ccatttgtat ataggatgag tttacagagc ggtgtgcaaa       240
```

```
gtgttttcca tctaagaaga agcagggagt ctcagtccaa gaaagagaag aataacacgg    300
tactggtaat gcacttatta gcacctgaca                                    330
```

<210> SEQ ID NO 45
<211> LENGTH: 694
<212> TYPE: DNA
<213> ORGANISM: Zea mays
<220> FEATURE:
<221> NAME/KEY: unsure
<222> LOCATION: (409)..(412)
<223> OTHER INFORMATION: n= a,t,c,or g
<220> FEATURE:
<221> NAME/KEY: unsure
<222> LOCATION: (416)..(417)
<223> OTHER INFORMATION: n= a,t,c, or g
<220> FEATURE:
<221> NAME/KEY: unsure
<222> LOCATION: (419)..(419)
<223> OTHER INFORMATION: n= a,t,c, or g
<220> FEATURE:
<221> NAME/KEY: unsure
<222> LOCATION: (564)..(568)
<223> OTHER INFORMATION: n= a,t,c, or g
<220> FEATURE:
<221> NAME/KEY: unsure
<222> LOCATION: (599)..(603)
<223> OTHER INFORMATION: n= a,t,c, or g
<220> FEATURE:
<221> NAME/KEY: unsure
<222> LOCATION: (623)..(627)
<223> OTHER INFORMATION: n= a,t,c, or g
<220> FEATURE:
<221> NAME/KEY: unsure
<222> LOCATION: (633)..(639)
<223> OTHER INFORMATION: n= a,t,c, or g
<220> FEATURE:
<221> NAME/KEY: unsure
<222> LOCATION: (644)..(649)
<223> OTHER INFORMATION: n= a,t,c, or g
<220> FEATURE:
<221> NAME/KEY: unsure
<222> LOCATION: (656)..(667)
<223> OTHER INFORMATION: n= a,t,c, or g
<220> FEATURE:
<221> NAME/KEY: unsure
<222> LOCATION: (669)..(672)
<223> OTHER INFORMATION: n= a,t,c, or g
<220> FEATURE:
<221> NAME/KEY: unsure
<222> LOCATION: (677)..(679)
<223> OTHER INFORMATION: n= a,t,c, or g
<220> FEATURE:
<221> NAME/KEY: unsure
<222> LOCATION: (681)..(683)
<223> OTHER INFORMATION: n= a,t,c, or g
<220> FEATURE:
<221> NAME/KEY: unsure
<222> LOCATION: (1)..(694)
<223> OTHER INFORMATION: unsure at all n locations

<400> SEQUENCE: 45

```
cagctggagc cacatcactg gagggtgccag caagcctcac aaggggaatg atcctagatg    60
gaaggcaatt catgctgtac gaactcgtga tagcgtgctt ggaatgagcc attttagact   120
actaaagcgt cttggttgtg gtgatattgg cagtgtttac ctctcagaat taagtggaac   180
tcggtgctac tttgcaatga aggtaatgga caaggcatcc ttggcaagta ggaaaaagtt   240
aaatagggct caaactgaaa gggagattct acagcttctt gaccacccat tcctcccaac   300
gttgtataca cattttgaaa ccgacaggtt ctcttgtttg gtgatggaat tctgtccagg   360
tggtgatctg catactttgc gacagagaca accaggaaag catttcatnn nnaccnnana   420
```

```
ggagatgctg tcggtttcaa aatgtgtata ccacgttggg aggaatgggt ggtcaagaag    480
ctgtagaatc tcccttcag tttgagccct atttaacttt ttcctacttg ccaaggatgc     540
cttgtccatt accttcattg cagnnnnncc gagttccacc ttaattctga gaggtaaann    600
nnncccatat caccacaccc aannnnnctt ttnnnnnnnt aaannnnnnc attcannnnn    660
nnnnnnncnn nncctannnc nnnaattgcc tttc                                694
```

```
<210> SEQ ID NO 46
<211> LENGTH: 248
<212> TYPE: DNA
<213> ORGANISM: Zea mays

<400> SEQUENCE: 46
ggcatacctg ttggaccagt gtatactgca agctgcctgt acaacaacca ttgggatcaa     60
agctcaattg catatcccaa tcgctcagct aaaggcattg gaaaaacaag tagaaagtct    120
agcagcttac tcagttgcat atcccaatcg ctcagctaaa ggcattattc ctagcatgct    180
gaaaagaaaa accaatccct gcaattttaa tgtcacgtga accatgtcag cattaagtta    240
acaggggg                                                             248
```

```
<210> SEQ ID NO 47
<211> LENGTH: 392
<212> TYPE: DNA
<213> ORGANISM: Zea mays
<220> FEATURE:
<221> NAME/KEY: unsure
<222> LOCATION: (2)..(2)
<223> OTHER INFORMATION: n= a,t,c, or g
<220> FEATURE:
<221> NAME/KEY: unsure
<222> LOCATION: (1)..(392)
<223> OTHER INFORMATION: unsure at all n locations

<400> SEQUENCE: 47
gngaattacg cacaaaaaca aaaatcacag gcagtaatgt gttgtttgaa ttcatacctg     60
gttgatgaaa agatctctga aaacacccga gcaattgacg acgacatcga tcctcgggcg    120
tccaagctcc tcaaggctga caggctccac acggttgaca cggccgaagg tgtcggcaac    180
tggccgaact ccaatcatcc acagcacctg gctagtgac tcaccatagg tcttgatgtt     240
atcggtgccc cacaggacaa gtgcgaccgt ctcagggtac ttgccgccat tgtcagcctt    300
ctgcctctcc aggagacggt ccacgacgat cttggcgctc ttcaaggcag ccgtggttgg    360
gatggcctgc ggatcgagag cgtggatgtt ct                                  392
```

```
<210> SEQ ID NO 48
<211> LENGTH: 28
<212> TYPE: DNA
<213> ORGANISM: artificial sequence
<220> FEATURE:
<223> OTHER INFORMATION: Other Information: Description of artificial
      sequence: synthetic primer

<400> SEQUENCE: 48
gctgacagca ctaatctaga gagagaga                                        28
```

```
<210> SEQ ID NO 49
<211> LENGTH: 24
<212> TYPE: DNA
<213> ORGANISM: artificial sequence
<220> FEATURE:
<223> OTHER INFORMATION: Other information: Description of artificial
      sequence: synthetic primer
```

```
<400> SEQUENCE: 49
tggcttctgt tgttgttcta gcat                                            24

<210> SEQ ID NO 50
<211> LENGTH: 24
<212> TYPE: DNA
<213> ORGANISM: artificial sequence
<220> FEATURE:
<223> OTHER INFORMATION: Other information: Description of artificial
      sequence: synthetic primer

<400> SEQUENCE: 50
aacagaagtt cacttggcaa caaa                                            24

<210> SEQ ID NO 51
<211> LENGTH: 22
<212> TYPE: DNA
<213> ORGANISM: artificial sequence
<220> FEATURE:
<223> OTHER INFORMATION: Other information: Description of artificial
      sequence: synthetic primer

<400> SEQUENCE: 51
tttgccaaag accagtgaag aa                                              22

<210> SEQ ID NO 52
<211> LENGTH: 23
<212> TYPE: DNA
<213> ORGANISM: artificial sequence
<220> FEATURE:
<223> OTHER INFORMATION: Other information: Description of artificial
      sequence: synthetic primer

<400> SEQUENCE: 52
caccacaaag acagggaaaa atg                                             23

<210> SEQ ID NO 53
<211> LENGTH: 27
<212> TYPE: DNA
<213> ORGANISM: artificial sequence
<220> FEATURE:
<223> OTHER INFORMATION: Other information: Description of artificial
      sequence: synthetic primer

<400> SEQUENCE: 53
gaatcctgag tttacctgat ttaatgg                                         27

<210> SEQ ID NO 54
<211> LENGTH: 27
<212> TYPE: DNA
<213> ORGANISM: artificial sequence
<220> FEATURE:
<223> OTHER INFORMATION: Other information: Description of artificial
      sequence: synthetic primer

<400> SEQUENCE: 54
gcaaagaaag agaagagatg aatacca                                         27

<210> SEQ ID NO 55
<211> LENGTH: 23
<212> TYPE: DNA
<213> ORGANISM: artificial sequence
<220> FEATURE:
<223> OTHER INFORMATION: Other information: Description of artificial
      sequence: synthetic primer
```

```
<400> SEQUENCE: 55
cattaccttt gctgccgtct cta                                          23

<210> SEQ ID NO 56
<211> LENGTH: 19
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 56
aggcaatact ttgagacaa                                               19

<210> SEQ ID NO 57
<211> LENGTH: 19
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 57
aggcaatact ttgacacaa                                               19

<210> SEQ ID NO 58
<211> LENGTH: 18
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 58
ctgaggtata agagctac                                                18

<210> SEQ ID NO 59
<211> LENGTH: 15
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 59
ccatacggac ccact                                                   15

<210> SEQ ID NO 60
<211> LENGTH: 13
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 60
tgggaggcaa ttc                                                     13

<210> SEQ ID NO 61
<211> LENGTH: 14
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 61
```

-continued aggcagttct tttg  14

<210> SEQ ID NO 62
<211> LENGTH: 15
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 62
agaagcagtg gcacc  15

<210> SEQ ID NO 63
<211> LENGTH: 15
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 63
agcagtagca cccac  15

<210> SEQ ID NO 64
<211> LENGTH: 16
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 64
tttttgtctc aaagta  16

<210> SEQ ID NO 65
<211> LENGTH: 16
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 65
tttttgtgtc aaagta  16

<210> SEQ ID NO 66
<211> LENGTH: 16
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 66
accatacgga cccact  16

<210> SEQ ID NO 67
<211> LENGTH: 16
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 67
accataccga cccact                                                    16

<210> SEQ ID NO 68
<211> LENGTH: 16
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 68
ggaggcagtt cttttg                                                    16

<210> SEQ ID NO 69
<211> LENGTH: 16
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 69
ggaggcaatt cttttg                                                    16

<210> SEQ ID NO 70
<211> LENGTH: 16
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 70
tgggtgctac tgcttc                                                    16

<210> SEQ ID NO 71
<211> LENGTH: 16
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 71
tgggtgccac tgcttc                                                    16

<210> SEQ ID NO 72
<211> LENGTH: 17
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 72
taaaaccttt ttttgtc                                                   17

<210> SEQ ID NO 73
<211> LENGTH: 17
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 73
ctgaggcaat actttga                                                   17

```
<210> SEQ ID NO 74
<211> LENGTH: 17
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 74
tggcaacaaa ccatacg                                                  17

<210> SEQ ID NO 75
<211> LENGTH: 17
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 75
tgaagaataa gtgggtc                                                  17

<210> SEQ ID NO 76
<211> LENGTH: 17
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 76
aaaatgttgg gaggcag                                                  17

<210> SEQ ID NO 77
<211> LENGTH: 17
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 77
aatgggcagc aaaagaa                                                  17

<210> SEQ ID NO 78
<211> LENGTH: 17
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 78
ccagctgcgt gggtgct                                                  17

<210> SEQ ID NO 79
<211> LENGTH: 17
<212> TYPE: DNA
<213> ORGANISM: artificial sequence
<220> FEATURE:
<223> OTHER INFORMATION: Other Information: Description of artificial
      sequence: synthetic probe

<400> SEQUENCE: 79
tctctatcag aagcagt                                                  17
```

METHODS AND COMPOSITIONS FOR SELECTING CORN PLANTS RESISTANT TO DIPLODIA EAR ROT

CROSS REFERENCE TO RELATED APPLICATIONS

This application is a divisional of U.S. application Ser. No. 15/784,421, filed Oct. 16, 2017, issued as U.S. Pat. No. 10,492,396, which is a divisional application of U.S. application Ser. No. 14/800,072, filed Jul. 15, 2015, issued as U.S. Pat. No. 9,788,505, which is a divisional application of U.S. application Ser. No. 13/524,716, filed Jun. 15, 2012, issued as U.S. Pat. No. 9,095,105, which is a divisional application of U.S. application Ser. No. 12/277,817, filed Nov. 25, 2008, issued as U.S. Pat. No. 8,222,481, which claims the benefit of U.S. Provisional Patent Application No. 60/990,413, filed Nov. 27, 2007, each of which are incorporated herein by reference in their entireties.

INCORPORATION OF SEQUENCE LISTING

A sequence listing is contained in the file named "46_21_55528C_Corrected.txt" which is 53687 bytes (measured in MS-Windows) and was created on Sep. 19, 2012, comprises 79 nucleotide sequences, and is herein incorporated by reference in its entirety.

FIELD OF INVENTION

The present invention relates to the field of plant breeding and disease resistance. More specifically, the present invention includes a method for breeding corn plants containing quantitative trait loci (QTL) that are associated with resistance to diplodia ear rot, a fungal disease associated with *Stenocarpella maydis* and *Stenocarpella macrospora*. The invention further includes germplasm and the use of germplasm containing QTL conferring disease resistance for introgression into elite germplasm in a breeding program for resistance to diplodia ear rot.

BACKGROUND OF INVENTION

Diplodia ear rot (DER) is a widespread fungal disease of corn caused by the pathogens *Stenocarpella maydis* and *Stenocarpella macrospora*. DER causes significant damage to crops with loss of yield and decrease in grain quality. In addition, when present in animal feed *S. maydis* has been associated with diplodiosis, a nervous disorder of livestock. DER has been problematic in many countries including the United States, South Africa, Brazil, Argentina, and Mexico. In South Africa, *S. maydis* is the most prevalent ear rot pathogen (Flett, B. B. and McLaren, N. W.; *Plant Disease* 78:587-589 (1994). Symptoms of DER include white fungal mycelium which starts at the base of an ear of corn and may cover the entire ear with pycnidia at the kernel base. Discoloration of kernels is another symptom of DER which may not be evident until kernels are removed from the ear. Symptoms are frequently not observable until the ear is opened. Phenotypic screening for ear rot infection is often difficult due to the need to hand harvest ears. Disease management strategies include such methods as crop rotation and fungicide application. However, genetic resistance to DER is the most promising method of controlling the disease. To date, a need exists in the art to develop improved methods to identify and select for genomic regions associated with tolerance or resistance to DER in order to breed DER resistant plants.

Studies have mapped QTL associated with resistance to other ear rot pathogens such as *Fusarium verticilliodes* and *Fusarium proliferatum*, the causative agents of *Fusarium* ear rot (Ali, M. L. et al., Genome 48: 521-533 (2005)), *Fusarium graminearum*, the causative agent of *Gibberella* ear rot (Robertson-Hoyt, L., Crop Sci. 46:1734-1743 (2006)), and *Aspergillus flavus*, the causative agent of *Aspergillus* ear rot (Busboom, K. N. and White, D. G., Amer. Phytopathological Soc. 94:1107-1115 (2004)). QTL associated with resistance to diplodia ear rot have not been disclosed before the priority date of this patent application.

SUMMARY OF INVENTION

The present invention provides QTL and single nucleotide polymorphism (SNP) markers associated with resistance to DER.

Breeding for corn plants resistant to DER can be greatly facilitated by the use of marker-assisted selection. Of the classes of genetic markers, single nucleotide polymorphisms (SNPs) have characteristics which make them preferential to other genetic markers in detecting, selecting for, and introgressing disease resistance in a corn plant. SNPs are preferred because technologies are available for automated, high-throughput screening of SNP markers, which can decrease the time to select for and introgress disease resistance in corn plants. Further, SNP markers are ideal because the likelihood that a particular SNP allele is derived from independent origins in the extant population of a particular species is very low. As such, SNP markers are useful for tracking and assisting introgression of disease resistance alleles, particularly in the case of disease resistance haplotypes.

The present invention provides and includes a method for screening and selecting a corn plant comprising one or more QTL associated with DER resistance that were derived from mapping populations that were phenotyped using endemic strains of *Stenocarpella maydis* and *Stenocarpella macrospora* and genotyped using single nucleotide polymorphisms (SNP) marker technology.

The present inventions provides a method of introgressing an allele into a corn plant comprising (a) crossing at least one DER resistant corn plant with at least one second corn plant in order to form a population, (b) genotyping with at least one second corn plant in the population with respect to a corn genomic nucleic acid marker selected from the group of SEQ ID NOs: 1 through 47, and (c) selecting from the population at least one corn plant comprising at least one genotype corresponding to a DER resistant corn plant. In certain embodiments of this method, the population formed, genotyped, and selected from can be a segregating population. The invention further provides an elite corn plant produced by such method.

The genotyping is effected in step (b) by determining the allelic state of at least one of the corn genomic DNA markers. The allelic state is determined by an assay which is selected from the group consisting of single base extension (SBE), allele-specific primer extension sequencing (ASPE), DNA sequencing, RNA sequencing, microarray-based analyses, universal PCR, allele specific extension, hybridization, mass spectrometry, ligation, extension-ligation, and Flap Endonuclease-mediated assays.

The invention further provides a method of introgressing an allele into a corn plant comprising: (a) crossing at least one DER resistant corn plant with at least one DER sensitive corn plant in order to form a population; (b) screening the population with at least one nucleic acid marker to determine if one or more corn plants from the population contains a DER resistance allele, wherein the DER resistance allele is an allele selected from the group consisting of 1, 2, 3, 4, 5, 6, 7, 8, 9, 10, 11, 12, 13, 14, 15, 16, 17, 18, 19, 20, 21, 22, 23, or 24 DER resistance loci. In certain embodiments of this method, the population formed, genotyped, and selected from can be a segregating population.

The invention provides an elite corn plant obtained by such method, the corn plant comprising a nucleic acid molecule selected from the group consisting of SEQ ID NOs: 1 through 47. The elite corn plant can exhibit a transgenic trait. Such transgenic trait is selected from the group consisting of herbicide tolerance, modified yield, insect control, fungal disease resistance, virus resistance, nematode resistance, bacterial disease resistance, mycoplasma disease resistance, starch production, starch modification, high oil production, modified oil production, modified fatty acid content, high protein production, germination and seedling growth control, plant growth and development, fruit ripening, enhanced animal and human nutrition, low raffinose, environmental stress resistance, increased digestibility, industrial enzymes, pharmaceutical peptides and secretable peptides and small molecules, improved digestibility, enzyme production, fiber production, improved processing traits, improved flavor, nitrogen fixation, hybrid seed production, reduced allergenicity, biopolymers, and biofuels among others. In one aspect, the herbicide tolerance is selected from the group consisting of glyphosate, dicamba, glufosinate, sulfonylurea, bromoxynil and norflurazon herbicides. These traits can be provided by methods of plant biotechnology as transgenes in corn.

The invention provides a substantially purified nucleic acid molecule for the detection of loci related to DER resistance comprising a nucleic acid molecule selected from the group consisting of SEQ ID NOs: 1 through 79 and complements thereof.

The invention further provides assays for detecting DER resistance loci in a corn plant.

Methods of identifying corn plants comprising at least one allele associated with diplodia ear rot (DER) resistance are also provided. In certain embodiments of these methods of identifying a corn plant comprising at least one allele associated with diplodia ear rot (DER) resistance or with DER tolerance in a corn plant, the methods comprise: (a) genotyping at least one corn plant with at least one corn genomic nucleic acid marker selected from the group of SEQ ID NOs: 1-46, and 47, and (b) selecting at least one corn plant comprising an allele of at least one of the nucleic acid markers that is associated with resistance or tolerance to DER. In certain embodiments, the at least one corn plant genotyped in step (a) and/or the at least one corn plant selected in step (b) is a corn plant from a population generated by a cross. In certain embodiments, genotyping in step (b) can be with at least five corn genomic nucleic acid markers are selected from the group of SEQ ID NOs: 1 through 47. In certain embodiments, the selected one or more corn plants exhibit at least tolerance to a DER-inducing fungus or exhibit at least resistance to a DER-inducing fungus. In embodiments where the population is generated by a cross, the cross can be of at least one DER resistant corn plant with at least one DER sensitive corn plant. In still other embodiments, the methods can further comprise the step (c) of assaying the selected corn plant for resistance to a DER-inducing fungus. In still other embodiments, the methods can further comprise the step of crossing the corn plant selected in step (b) to another corn plant. In still other embodiments, the methods can further comprise the step of obtaining seed from the corn plant selected in step (b). In certain embodiments of the methods, resistance or tolerance is to a DER-inducing fungus selected from the group consisting of *Stenocarpella maydis* and *Stenocarpella macrospora*.

Also provided herein are corn plants obtained by any of these methods of identifying corn plants comprising at least one allele associated with diplodia ear rot (DER) resistance. In certain embodiments, corn plants obtained by these methods can comprise an allele of at least one nucleic acid molecule selected from the group consisting of SEQ ID NOs: 1 through 47 that is associated with resistance or tolerance to DER, and wherein the corn plant exhibits at least tolerance to a DER-inducing fungus or at least resistance to a DER-inducing fungus. In certain embodiments, corn plants obtained by these methods are elite corn plants.

Methods of introgressing a diplodia ear rot (DER) resistance locus into a corn plant are also provided. In certain embodiments, these methods of introgressing a diplodia ear rot (DER) resistance locus into a corn plant comprise: (a) screening a population with at least one nucleic acid marker to determine if one or more corn plants from the population contains a diplodia ear rot (DER) resistance locus, wherein the DER resistance locus is selected from the group consisting of 1, 2, 3, 4, 5, 6, 7, 8, 9, 10, 11, 12, 13, 14, 15, 16, 17, 18, 19, 20, 21, 22, 23, or 24 DER resistant loci, and (b) selecting from the population at least one corn plant comprising an allele of the marker associated with the DER resistance locus. In certain embodiments of these methods, at least one of the markers is as provided in FIG. 1, 2, 3, 4, 5, 6, or Table 4. In certain embodiments of these methods, at least one of the markers is located within 5 cM, 2 cM, or 1 cM of the resistant allele. In other embodiments, at least one of the markers is located within 2 cM, or 1 cM of the resistant allele. In certain embodiments of these methods, at least one of the markers is located within 100 Kb of the resistance allele. In other embodiments, at least one of the markers is located within 1 Mb, or 1 Kb of the resistant allele. In certain embodiments of these methods, the population is a segregating population. In certain embodiments of these methods, at least one of the markers exhibits a LOD score of greater than 2.0 with the DER resistance locus. In other embodiments, at least one of the markers exhibits a LOD score of greater than 3.0 or greater than 4.0 with the DER resistance locus. In certain embodiments of these methods, at least one of the markers is selected from the group consisting of SEQ ID NO:1-46, and 47.

Also provided herein are corn plants obtained by any of these methods of introgressing a diplodia ear rot (DER) resistance locus into a corn plant. In certain embodiments, a corn plant obtained by these methods can comprise an allele of at least one of nucleic acid marker selected from the group consisting of SEQ ID NO:1-46, and 47 that is associated with resistance to DER or with tolerance to DER. In certain embodiments, a corn plant obtained by these methods can exhibit at least tolerance to a DER-inducing fungus. In certain embodiments, a corn plant obtained by these methods can exhibit at least resistance to a DER-inducing fungus. In certain embodiments, corn plants obtained by these methods are at least tolerant or at least resistant to a DER-inducing fungus is selected from the group consisting of *Stenocapella macrospora* and *Stenocarpella maydis*.

Also provided are isolated nucleic acid molecules for detecting a molecular marker representing a polymorphism in corn DNA, wherein the nucleic acid molecule comprises at least 15 nucleotides that include or are adjacent to the polymorphism, wherein the nucleic acid molecule is at least 90 percent identical to a sequence of the same number of consecutive nucleotides in either strand of DNA that include or are adjacent to the polymorphism, and wherein the molecular marker is selected from the group consisting of SEQ ID NOs: 1 through 47. In certain embodiments, the nucleic acid can further comprises a detectable label or provide for incorporation of a detectable label. In certain embodiments, the nucleic acid molecule hybridizes to at least one allele of the molecular marker under stringent hybridization conditions. In certain embodiments, the molecular marker is SEQ ID NO: 27 and the isolated nucleic acid is an oligonucleotide that is at least 90% identical to SEQ ID NOs: 56, 57, 64, 65, 72, or 73. In certain embodiments, the molecular marker is SEQ ID NO: 28 and the nucleic acid is an oligonucleotide that is at least 90% identical to SEQ ID NOs: 58, 59, 66, 67, 74, or 75. In certain embodiments, the molecular marker is SEQ ID NO: 5 and the nucleic acid is an oligonucleotide that is at least 90% identical to SEQ ID NOs: 60, 61, 68, 69, 76, or 77. In certain embodiments, the molecular marker is SEQ ID NO: 6 and the nucleic acid is an oligonucleotide that is at least 90% identical to SEQ ID NOs: 62, 63, 70, 71, 78, or 79.

Brief Description of Nucleic Acid Sequences

SEQ ID NO: 1 is a genomic sequence derived from *Zea mays* L associated with DER resistance locus 1.

SEQ ID NO: 2 is a genomic sequence derived from *Zea mays* L associated with DER resistance locus 1.

SEQ ID NO: 3 is a genomic sequence derived from *Zea mays* L associated with DER resistance locus 2.

SEQ ID NO: 4 is a genomic sequence derived from *Zea mays* L associated with DER resistance locus 2.

SEQ ID NO: 5 is a genomic sequence derived from *Zea mays* L associated with DER resistance locus 3.

SEQ ID NO: 6 is a genomic sequence derived from *Zea mays* L associated with DER resistance locus 3.

SEQ ID NO: 7 is a genomic sequence derived from *Zea mays* L associated with DER resistance locus 4.

SEQ ID NO: 8 is a genomic sequence derived from *Zea mays* L associated with DER resistance locus 5.

SEQ ID NO: 9 is a genomic sequence derived from *Zea mays* L associated with DER resistance locus 4.

SEQ ID NO: 10 is a genomic sequence derived from *Zea mays* L associated with DER resistance locus 5.

SEQ ID NO: 11 is a genomic sequence derived from *Zea mays* L associated with DER resistance locus 6.

SEQ ID NO: 12 is a genomic sequence derived from *Zea mays* L associated with DER resistance locus 6.

SEQ ID NO: 13 is a genomic sequence derived from *Zea mays* L associated with DER resistance locus 7.

SEQ ID NO: 14 is a genomic sequence derived from *Zea mays* L associated with DER resistance locus 7.

SEQ ID NO: 15 is a genomic sequence derived from *Zea mays* L associated with DER resistance locus 8.

SEQ ID NO: 16 is a genomic sequence derived from *Zea mays* L associated with DER resistance locus 8.

SEQ ID NO: 17 is a genomic sequence derived from *Zea mays* L associated with DER resistance locus 9.

SEQ ID NO: 18 is a genomic sequence derived from *Zea mays* L associated with DER resistance locus 10.

SEQ ID NO: 19 is a genomic sequence derived from *Zea mays* L associated with DER resistance locus 9.

SEQ ID NO: 20 is a genomic sequence derived from *Zea mays* L associated with DER resistance locus 10.

SEQ ID NO: 21 is a genomic sequence derived from *Zea mays* L associated with DER resistance locus 11.

SEQ ID NO: 22 is a genomic sequence derived from *Zea mays* L associated with DER resistance locus 12.

SEQ ID NO: 23 is a genomic sequence derived from *Zea mays* L associated with DER resistance locus 11.

SEQ ID NO: 24 is a genomic sequence derived from *Zea mays* L associated with DER resistance locus 12.

SEQ ID NO: 25 is a genomic sequence derived from *Zea mays* L associated with DER resistance locus 13.

SEQ ID NO: 26 is a genomic sequence derived from *Zea mays* L associated with DER resistance locus 13.

SEQ ID NO: 27 is a genomic sequence derived from *Zea mays* L associated with DER resistance locus 14.

SEQ ID NO: 28 is a genomic sequence derived from *Zea mays* L associated with DER resistance locus 14.

SEQ ID NO: 29 is a genomic sequence derived from *Zea mays* L associated with DER resistance locus 15.

SEQ ID NO: 30 is a genomic sequence derived from *Zea mays* L associated with DER resistance locus 16.

SEQ ID NO: 31 is a genomic sequence derived from *Zea mays* L associated with DER resistance locus 15.

SEQ ID NO: 32 is a genomic sequence derived from *Zea mays* L associated with DER resistance locus 16.

SEQ ID NO: 33 is a genomic sequence derived from *Zea mays* L associated with DER resistance locus 17.

SEQ ID NO: 34 is a genomic sequence derived from *Zea mays* L associated with DER resistance locus 17.

SEQ ID NO: 35 is a genomic sequence derived from *Zea mays* L associated with DER resistance locus 18.

SEQ ID NO: 36 is a genomic sequence derived from *Zea mays* L associated with DER resistance locus 19.

SEQ ID NO: 37 is a genomic sequence derived from *Zea mays* L associated with DER resistance locus 18.

SEQ ID NO: 38 is a genomic sequence derived from *Zea mays* L associated with DER resistance locus 20.

SEQ ID NO: 39 is a genomic sequence derived from *Zea mays* L associated with DER resistance locus 20.

SEQ ID NO: 40 is a genomic sequence derived from *Zea mays* L associated with DER resistance locus 21.

SEQ ID NO: 41 is a genomic sequence derived from *Zea mays* L associated with DER resistance locus 21.

SEQ ID NO: 42 is a genomic sequence derived from *Zea mays* L associated with DER resistance locus 22.

SEQ ID NO: 43 is a genomic sequence derived from *Zea mays* L associated with DER resistance locus 22.

SEQ ID NO: 44 is a genomic sequence derived from *Zea mays* L associated with DER resistance locus 23.

SEQ ID NO: 45 is a genomic sequence derived from *Zea mays* L associated with DER resistance locus 23.

SEQ ID NO: 46 is a genomic sequence derived from *Zea mays* L associated with DER resistance locus 24.

SEQ ID NO: 47 is a genomic sequence derived from *Zea mays* L associated with DER resistance locus 24.

SEQ ID NO: 48 is a forward PCR primer for the amplification of SEQ ID NO: 27.

SEQ ID NO: 49 is a reverse PCR primer for the amplification of SEQ ID NO: 27.

SEQ ID NO: 50 is a forward PCR primer for the amplification of SEQ ID NO: 28.

SEQ ID NO: 51 is a reverse PCR primer for the amplification of SEQ ID NO: 28.

SEQ ID NO: 52 is a forward PCR primer for the amplification of SEQ ID NO: 5.

SEQ ID NO: 53 is a reverse PCR primer for the amplification of SEQ ID NO: 5.

SEQ ID NO: 54 is a forward PCR primer for the amplification of SEQ ID NO: 6.

SEQ ID NO: 55 is a reverse PCR primer for the amplification of SEQ ID NO: 6.

SEQ ID NO: 56 is a probe for the detection of the SNP of SEQ ID NO: 27.

SEQ ID NO: 57 is a second probe for the detection of the SNP of SEQ ID NO: 27.

SEQ ID NO: 58 is a probe for the detection of the SNP of SEQ ID NO: 28.

SEQ ID NO: 59 is a second probe for the detection of the SNP of SEQ ID NO: 28.

SEQ ID NO: 60 is a probe for the detection of the SNP of SEQ ID NO: 5.

SEQ ID NO: 61 is a second probe for the detection of the SNP of SEQ ID NO: 5.

SEQ ID NO: 62 is a probe for the detection of the SNP of SEQ ID NO: 6.

SEQ ID NO: 63 is a second probe for the detection of the SNP of SEQ ID NO: 6.

SEQ ID NO: 64 is a third probe for the detection of the SNP of SEQ ID NO: 27.

SEQ ID NO: 65 is a fourth probe for the detection of the SNP of SEQ ID NO: 27.

SEQ ID NO: 66 is a third probe for the detection of the SNP of SEQ ID NO: 28.

SEQ ID NO: 67 is a fourth probe for the detection of the SNP of SEQ ID NO: 28.

SEQ ID NO: 68 is a third probe for the detection of the SNP of SEQ ID NO: 5.

SEQ ID NO: 69 is a fourth probe for the detection of the SNP of SEQ ID NO: 5.

SEQ ID NO: 70 is a third probe for the detection of the SNP of SEQ ID NO: 6.

SEQ ID NO: 71 is a fourth probe for the detection of the SNP of SEQ ID NO: 6.

SEQ ID NO: 72 is a fifth probe for the detection of the SNP of SEQ ID NO: 27.

SEQ ID NO: 73 is a sixth probe for the detection of the SNP of SEQ ID NO: 27.

SEQ ID NO: 74 is a fifth probe for the detection of the SNP of SEQ ID NO: 28.

SEQ ID NO: 75 is a sixth probe for the detection of the SNP of SEQ ID NO: 28.

SEQ ID NO: 76 is a fifth probe for the detection of the SNP of SEQ ID NO: 5.

SEQ ID NO: 77 is a sixth probe for the detection of the SNP of SEQ ID NO: 5.

SEQ ID NO: 78 is a fifth probe for the detection of the SNP of SEQ ID NO: 6.

SEQ ID NO: 79 is a sixth probe for the detection of the SNP of SEQ ID NO: 6.

BRIEF DESCRIPTION OF THE DRAWINGS

The accompanying drawings, which are incorporated in and form a part of the specification, illustrate the embodiments of the present invention and together with the description, serve to explain the principles of the invention.

In the drawings:

FIG. 1. Displays DER Resistance Loci associated with DER resistance in CV183/CV174+01HGI4. In the final column indicating Geography, SA is South Africa, AR is Argentina, and U.S. is the United States of America.

FIG. 2. Displays DER Resistance Loci (QTL) and SNP markers associated with DER resistance in the CV128/CV162 population in Central Brazil.

FIG. 3. Displays DER Resistance Loci (QTL) and SNP markers associated with DER resistance in the CV128/CV162 population in Central Brazil. Data were from a CV128*2/CV162 Mapping Population in Central Brazil with *S. macrospora*.

FIG. 4. Displays DER Resistance Loci (QTL) and SNP markers associated with DER resistance in the CV128/CV162 population in Central Brazil. Data are for a CV128*2/CV162 Mapping Population in Central Brazil with *S. maydis*.

FIG. 5. Displays Resistance Loci (QTL) and SNP markers associated with DER resistance in the CV162/CV129+CV128 mapping population in Central Brazil. Under "Effect", "dom" represents "dominant".

FIG. 6. Displays Resistance Loci (QTL) and SNP markers associated with DER resistance in the CV162/CV129+CV128 population.

DETAILED DESCRIPTION OF THE INVENTION

The definitions and methods provided herein define the present invention and guide those of ordinary skill in the art in the practice of the present invention. Unless otherwise noted, terms are to be understood according to conventional usage by those of ordinary skill in the relevant art. Definitions of common terms in molecular biology may also be found in Alberts et al., Molecular Biology of The Cell, $3^{rd}$ Edition, Garland Publishing, Inc.: New York, 1994; Rieger et al., Glossary of Genetics: Classical and Molecular, 5th edition, Springer-Verlag: New York, 1991; and Lewin, Genes V, Oxford University Press: New York, 1994. The nomenclature for DNA bases as set forth at 37 CFR § 1.822 is used.

As used herein, “resistance allele” means the isolated nucleic acid sequence that includes the polymorphic allele associated with resistance to *Stenocarpella maydis* and *Stenocarpella macrospora.*

As used herein, “resistance allele” means the isolated nucleic acid sequence that includes the polymorphic allele associated with resistance to *Stenocarpella maydis* and *Stenocarpella macrospora.*

An “allele” refers to an alternative sequence at a particular locus; the length of an allele can be as small as 1 nucleotide base, but is typically larger. Allelic sequence can be amino acid sequence or nucleic acid sequence.

A “locus” is a short sequence that is usually unique and usually found at one particular location in the genome by a point of reference; e.g., a short DNA sequence that is a gene, or part of a gene or intergenic region. A locus of this invention can be a unique PCR product at a particular location in the genome. The loci of this invention comprise one or more polymorphisms; i.e., alternative alleles present in some individuals.

As used herein, “polymorphism” means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism includes a single nucleotide polymorphism (SNP), a simple sequence repeat (SSR) and indels, which are insertions and deletions. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the later may be associated with rare but important phenotypic variation.

As used herein, "marker" means a polymorphic nucleic acid sequence or nucleic acid feature. A "polymorphism" is a variation among individuals in sequence, particularly in DNA sequence, or feature, such as a transcriptional profile or methylation pattern. Useful polymorphisms include single nucleotide polymorphisms (SNPs), insertions or deletions in DNA sequence (Indels), simple sequence repeats of DNA sequence (SSRs) a restriction fragment length polymorphism, a haplotype, and a tag SNP. A genetic marker, a gene, a DNA-derived sequence, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms. In a broader aspect, a "marker" can be a detectable characteristic that can be used to discriminate between heritable differences between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics.

As used herein, "marker assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "typing" refers to any method whereby the specific allelic form of a given corn genomic polymorphism is determined. For example, a single nucleotide polymorphism (SNP) is typed by determining which nucleotide is present (i.e. an A, G, T, or C). Insertion/deletions (Indels) are determined by determining if the Indel is present. Indels can be typed by a variety of assays including, but not limited to, marker assays.

As used herein, the phrase "immediately adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "immediately adjacent" to the polymorphism.

As used herein, "interrogation position" refers to a physical position on a solid support that can be queried to obtain genotyping data for one or more predetermined genomic polymorphisms.

As used herein, "consensus sequence" refers to a constructed DNA sequence which identifies SNP and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

As used herein, the term "single nucleotide polymorphism," also referred to by the abbreviation "SNP," means a polymorphism at a single site wherein the polymorphism constitutes a single base pair change, an insertion of one or more base pairs, or a deletion of one or more base pairs.

As used herein, "genotype" means the genetic component of the phenotype and it can be indirectly characterized using markers or directly characterized by nucleic acid sequencing. Suitable markers include a phenotypic character, a metabolic profile, a genetic marker, or some other type of marker. A genotype may constitute an allele for at least one genetic marker locus or a haplotype for at least one haplotype window. In some embodiments, a genotype may represent a single locus and in others it may represent a genome-wide set of loci. In another embodiment, the genotype can reflect the sequence of a portion of a chromosome, an entire chromosome, a portion of the genome, and the entire genome.

As used herein, "phenotype" means the detectable characteristics of a cell or organism which are a manifestation of gene expression.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, "linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are the to be "genetically linked" when they are in linkage disequilibrium.

As used herein, "quantitative trait locus (QTL)" means a locus that controls to some degree numerically representable traits that are usually continuously distributed.

As used herein, the term "inbred" means a line that has been bred for genetic homogeneity.

As used herein, the term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines.

As used herein, the term "tester" means a line used in a testcross with another line wherein the tester and the lines tested are from different germplasm pools. A tester may be isogenic or nonisogenic.

As used herein, the term "corn" means *Zea mays* or maize and includes all plant varieties that can be bred with corn, including wild maize species.

As used herein, the term "comprising" means "including but not limited to".

As used herein, the term "elite line" means any line that has resulted from breeding and selection for superior agronomic performance. An elite plant is any plant from an elite line.

To the extent to which any of the preceding definitions is inconsistent with definitions provided in any patent or non-patent reference incorporated herein or in any reference found elsewhere, it is understood that the preceding definition will be used herein.

In general, these compositions and methods can be used to genotype corn plants from the genus Zea. More specifically, corn plants from the species Zea mays and the subspecies Zea mays L. ssp. Mays can be genotyped using these compositions and methods. In an additional aspect, the corn plant is from the group Zea mays L. subsp. mays Indentata, otherwise known as dent corn. In another aspect, the corn plant is from the group Zea mays L. subsp. mays Indurata, otherwise known as flint corn. In another aspect, the corn plant is from the group Zea mays L. subsp. mays Saccharata, otherwise known as sweet corn. In another aspect, the corn plant is from the group Zea mays L. subsp. mays Amylacea, otherwise known as flour corn. In a further aspect, the corn plant is from the group Zea mays L. subsp. mays Everta, otherwise known as pop corn. Zea or corn plants that can be genotyped with the compositions and methods described herein include hybrids, inbreds, partial inbreds, or members of defined or undefined populations.

Plants of the present invention can be a corn plant that is very resistant, resistant, substantially resistant, mid-resistant, comparatively resistant, partially resistant, mid-susceptible, or susceptible.

In a preferred aspect, the present invention provides a corn plant to be assayed for resistance or susceptibility to DER by any method to determine whether a corn plant is very resistant, resistant, substantially resistant, mid-resistant, comparatively resistant, partially resistant, mid-susceptible, or susceptible.

Plants are artificially inoculated with either a mixture containing Stenocarpella maydis and Stenocarpella macrospora isolate or the isolates of either pathogen. Methods of inoculation include deposition of fungal spores in the grain stalk, the whorl method (Flett and McLaren; Plant Disease 78:587-589 (1994); Bensch, M. J., S. Afr. J. Plant Soil 12: 172-174), and the method according to Chambers (Plant Disease 72:529-531 (1988)), Klapproth and Hawk (Plant Disease 75: 1057-1060 (1991), and Villena (1969). Phenotyping for DER is done by the following methods. Resistance or susceptibility is determined after hand harvesting ears. In one method, percentage of rotten ears of total ears in a plot is calculated and used as phenotypic data. In another method, ears are shelled after harvesting. Total grain weight and rotten grain weight are determined. Percentage rotten grain is then used as phenotypic data.

In another aspect, the corn plant can show a comparative resistance compared to a non-resistant control corn plant. In this aspect, a control corn plant will preferably be genetically similar except for the DER resistance allele or alleles in question. Such plants can be grown under similar conditions with equivalent or near equivalent exposure to the pathogen.

A disease resistance QTL of the present invention may be introduced into an elite corn inbred line. An "elite line" is any line that has resulted from breeding and selection for superior agronomic performance.

A DER resistance QTL of the present invention may also be introduced into an elite corn plant comprising one or more transgenes conferring herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. In one aspect, the herbicide tolerance is selected from the group consisting of glyphosate, dicamba, glufosinate, sulfonylurea, bromoxynil and norflurazon herbicides. These traits can be provided by methods of plant biotechnology as transgenes in corn.

A disease resistance QTL allele or alleles can be introduced from any plant that contains that allele (donor) to any recipient corn plant. In one aspect, the recipient corn plant can contain additional DER resistance loci. In another aspect, the recipient corn plant can contain a transgene. In another aspect, while maintaining the introduced QTL, the genetic contribution of the plant providing the disease resistance QTL can be reduced by back-crossing or other suitable approaches. In one aspect, the nuclear genetic material derived from the donor material in the corn plant can be less than or about 50%, less than or about 25%, less than or about 13%, less than or about 5%, 3%, 2% or 1%, but that genetic material contains the DER resistance locus or loci of interest.

It is further understood that a corn plant of the present invention may exhibit the characteristics of any relative maturity group. In an aspect, the maturity group is selected from the group consisting of RM90-95, RM 95-100, RM 100-105, RM 105-110, RM 110-115, and RM 115-120.

An allele of a QTL can, of course, comprise multiple genes or other genetic factors even within a contiguous genomic region or linkage group, such as a haplotype. As used herein, an allele of a disease resistance locus can therefore encompass more than one gene or other genetic factor where each individual gene or genetic component is also capable of exhibiting allelic variation and where each gene or genetic factor is also capable of eliciting a phenotypic effect on the quantitative trait in question. In an aspect of the present invention the allele of a QTL comprises one or more genes or other genetic factors that are also capable of exhibiting allelic variation. The use of the term "an allele of a QTL" is thus not intended to exclude a QTL that comprises more than one gene or other genetic factor. Specifically, an "allele of a QTL" in the present invention can denote a haplotype within a haplotype window wherein a phenotype can be disease resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. As used herein, an allele is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular DER locus or for a particular polymorphic marker.

The present invention also provides for parts of the plants of the present invention. Plant parts, without limitation, include seed, endosperm, ovule and pollen. In a particularly preferred aspect of the present invention, the plant part is a seed.

The present invention also provides a container of corn in which greater than 50%, 60%, 70%, 80%, 90%, 95%, or 99% of the seeds comprising 1, 2, 3, 4, 5, 6, 7, 8, 9, 10, 11, 12, 13, 14, 15, 16, 17, 18, 19, 20, 21, 22, 23, or 24 DER resistance loci. The container of corn seeds can contain any number, weight, or volume of seeds. For example, a container can contain at least, or greater than, about 10, 25, 50, 100, 200, 300, 400, 500, 600, 700, 800, 900, 1000, 1500, 2000, 2500, 3000, 3500, 4000 or more seeds. In another aspect, a container can contain about, or greater than about, 1 gram, 5 grams, 10 grams, 15 grams, 20 grams, 25 grams, 50 grams, 100 grams, 250 grams, 500 grams, or 1000 grams of seeds. Alternatively, the container can contain at least, or greater than, about 0 ounces, 1 ounce, 5 ounces, 10 ounces, 1 pound, 2 pounds, 3 pounds, 4 pounds, 5 pounds, 10 pounds, 15 pounds, 20 pounds, 25 pounds, or 50 pounds or more seeds.

Containers of corn seeds can be any container available in the art. For example, a container can be a box, a bag, a can, a packet, a pouch, a tape roll, a pail, or a tube.

In another aspect, the seeds contained in the containers of corn seeds can be treated or untreated corn seeds. In one aspect, the seeds can be treated to improve germination, for example, by priming the seeds, or by disinfection to protect against seed-born pathogens. In another aspect, seeds can be coated with any available coating to improve, for example, plantability, seed emergence, and protection against seed-born pathogens. Seed coating can be any form of seed coating including, but not limited to, pelleting, film coating, and encrustments.

Plants or parts thereof of the present invention may also be grown in culture and regenerated. Methods for the regeneration of *Zea mays* plants from various tissue types and methods for the tissue culture of *Zea mays* are known in the art (for example, Bhaskaran et al., 1990 Crop Sci. 30:1328-1336). Regeneration techniques for plants such as *Zea mays* can use as the starting material a variety of tissue or cell types. With *Zea mays* in particular, regeneration processes have been developed that begin with certain differentiated tissue types such as meristems, (Sairam et al., 2003 Genome 46:323-3). Regeneration of mature *Zea mays* plants from tissue culture by organogenesis and embryogenesis has also been reported (Wang 1987 Plant Cell. Rep. 6:360-362; Chang 1983 Plant Cell. Rep. 2:18-185; Green et al., 1975 Crop Sci. 15:417-421). Recently, regeneration of corn from split seeds was also reported (Al-Abed et al., 2006 Planta 223:1355-1366).

The present invention also provides a disease resistant corn plant selected for by screening for disease resistance or susceptibility in the corn plant, the selection comprising interrogating genomic nucleic acids for the presence of a marker molecule that is genetically linked to an allele of a QTL associated with disease resistance in the corn plant, where the allele of a QTL is also located on a linkage group associated with DER resistance.

The present invention provides a method of introgressing an allele associated with diplodia ear rot (DER) resistance into a corn plant comprising (a) crossing at least one DER resistant corn plant with at least one second corn plant in order to form a population, (b) genotyping with at least one second corn plant in the population with respect to a corn genomic nucleic acid marker selected from the group of SEQ ID NOs: 1 through 47, and (c) selecting from the population at least one corn plant comprising at least one genotype corresponding to a DER resistant corn plant.

The present invention also includes a method of introgressing an allele into a corn plant comprising: (a) crossing at least one DER resistant corn plant with at least one DER sensitive corn plant in order to form a population; (b) screening the population with one or more nucleic acid markers to determine if one or more corn plants from the population contains a DER resistance allele, wherein the DER resistance allele is an allele selected from the group consisting of DER resistance locus 1, 2, 3, 4, 5, 6, 7, 8, 9, 10, 11, 12, 13, 14, 15, 16, 17, 18, 19, 20, 21, 22, 23, or DER resistance locus 24. In certain embodiments, these methods can further comprise the step of selecting a plant that comprises one or more DER resistance loci selected from the group consisting of DER resistance locus 1, 2, 3, 4, 5, 6, 7, 8, 9, 10, 11, 12, 13, 14, 15, 16, 17, 18, 19, 20, 21, 22, 23, or DER resistance locus 24. In certain embodiments of this method, the population formed, screened, and/or selected from can be a segregating population.

The present invention includes isolated nucleic acid molecules. Such molecules include those nucleic acid molecules capable of detecting a polymorphism genetically or physically linked to a DER resistance locus. Such molecules can be referred to as markers. Additional markers can be obtained that are linked to DER resistance locus 1, 2, 3, 4, 5, 6, 7, 8, 9, 10, 11, 12, 13, 14, 15, 16, 17, 18, 19, 20, 21, 22, 23, or 24 by available techniques. In one aspect, the nucleic acid molecule is capable of detecting the presence or absence of a marker located less than 30, 20, 10, 5, 2, or 1 centimorgans from a DER resistance locus. Exemplary nucleic acid molecules with corresponding map positions are provided in U.S. Patent Application No. 2005/0218305 and U.S. patent application Ser. Nos. 11/504,538 and 60/930,609. In another aspect, a marker exhibits a LOD score of 2 or greater, 3 or greater, or 4 or greater with DER, measuring using Qgene™ Version 2.23 (Department of Plant Breeding and Biometry, 266 Emerson Hall, Cornell University, Ithaca, N.Y., 1996) and default parameters. In another aspect, the nucleic acid molecule is capable of detecting a marker in a locus selected from the group DER resistance locus 1, 2, 3, 4, 5, 6, 7, 8, 9, 10, 11, 12, 13, 14, 15, 16, 17, 18, 19, 20, 21, 22, 23, or 24. In a further aspect, a nucleic acid molecule is selected from the group consisting of SEQ ID NO: 1 through SEQ ID NO: 79 fragments thereof, complements thereof, and nucleic acid molecules capable of specifically hybridizing to one or more of these nucleic acid molecules.

In a preferred aspect, a nucleic acid molecule of the present invention includes those that will specifically hybridize to one or more of the nucleic acid molecules set forth in SEQ ID NO: 1 through SEQ ID NO: 79 or complements thereof or fragments of either under moderately stringent conditions, for example at about 2.0×SSC and about 65° C. In a particularly preferred aspect, a nucleic acid of the present invention will specifically hybridize to one or more of the nucleic acid molecules set forth in SEQ ID NO: 1 through SEQ ID NO: 79 or complements or fragments of either under high stringency conditions. In one aspect of the present invention, a preferred marker nucleic acid molecule of the present invention has the nucleic acid sequence set forth in SEQ ID NO: 1 through SEQ ID NO: 79 or complements thereof or fragments of either. In another aspect of the present invention, a preferred marker nucleic acid molecule of the present invention shares between 80% and 100% or 90% and 100% sequence identity with the nucleic acid sequences set forth in SEQ ID NO: 1 through SEQ ID NO: 79 or complements thereof or fragments of either. In a further aspect of the present invention, a preferred marker nucleic acid molecule of the present invention shares between 95% and 100% sequence identity with the sequences set forth in SEQ ID NO: 1 through SEQ ID NO: 79 or complements thereof or fragments of either. In a more preferred aspect of the present invention, a preferred marker nucleic acid molecule of the present invention shares between 98% and 100% sequence identity with the nucleic acid sequence set forth in SEQ ID NO: 1 through SEQ ID NO: 79 or complement thereof or fragments of either.

Nucleic acid molecules or fragments thereof are capable of specifically hybridizing to other nucleic acid molecules under certain circumstances. As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, molecules that are exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual*, 2nd *Edition*, Cold Spring Harbor Press, Cold Spring Harbor, N.Y. (1989), and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa 1984 Nucl. Acids Res. 12:203-213; and Wetmur et al., 1968 J. Mol. Biol. 31:349-370. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5×Denhardt's, 100 µg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA, RNA, or cDNA fragments.

A fragment of a nucleic acid molecule can be any sized fragment and illustrative fragments include fragments of nucleic acid sequences set forth in SEQ ID NO: 1 through SEQ ID NO: 79 and complements thereof. In one aspect, a fragment can be between 15 and 25, 15 and 30, 15 and 40, 15 and 50, 15 and 100, 20 and 25, 20 and 30, 20 and 40, 20 and 50, 20 and 100, 25 and 30, 25 and 40, 25 and 50, 25 and 100, 30 and 40, 30 and 50, and 30 and 100. In another aspect, the fragment can be greater than 10, 15, 20, 25, 30, 35, 40, 50, 100, or 250 nucleotides.

Additional genetic markers can be used to select plants with an allele of a QTL associated with fungal disease resistance of DER of the present invention. Examples of public marker databases include, for example: Maize Genome Database, Agricultural Research Service, United States Department of Agriculture. Genetic markers of the present invention include "dominant" and "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers, such as single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al., 2003 Gen. Res. 13:513-523), microarray transcription profiles, DNA-derived sequences, and RNA-derived sequences that are genetically linked to or correlated with alleles of a QTL of the present invention can be utilized.

In one embodiment, nucleic acid-based analyses for the presence or absence of the genetic polymorphism can be used for the selection of seeds in a breeding population. A wide variety of genetic markers for the analysis of genetic polymorphisms are available and known to those of skill in the art. The analysis may be used to select for genes, QTL, alleles, or genomic regions (haplotypes) that comprise or are linked to a genetic marker.

Herein, nucleic acid analysis methods are known in the art and include, but are not limited to, PCR-based detection methods (for example, TaqMan assays), microarray methods, and nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al., 1986 Cold Spring Harbor Symp. Quant. Biol. 51:263-273; European Patent No. 50,424; European Patent No. 84,796; European Patent No. 258,017; European Patent No. 237,362; European Patent No. 201,184; U.S. Pat. Nos. 4,683,202; 4,582,788; and 4,683,194), using primer pairs that are capable of hybridizing to the proximal sequences that define a polymorphism in its double-stranded form.

Polymorphisms in DNA sequences can be detected or typed by a variety of effective methods well known in the art including, but not limited to, those disclosed in U.S. Pat. Nos. 5,468,613 and 5,217,863; 5,210,015; 5,876,930; 6,030,787; 6,004,744; 6,013,431; 5,595,890; 5,762,876; 5,945,283; 5,468,613; 6,090,558; 5,800,944; and 5,616,464, all of which are incorporated herein by reference in their entireties. However, the compositions and methods of this invention can be used in conjunction with any polymorphism typing method to type polymorphisms in corn genomic DNA samples. These corn genomic DNA samples used include but are not limited to, corn genomic DNA isolated directly from a corn plant, cloned corn genomic DNA, or amplified corn genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464 employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of corn genomic DNA which flanks a region containing the polymorphism to be assayed. Following amplification of the region of the corn genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In a preferred method for detecting polymorphisms, SNPs and Indels can be detected by methods disclosed in U.S. Pat. Nos. 5,210,015; 5,876,930; and 6,030,787 in which an oligonucleotide probe having a 5'fluorescent reporter dye and a 3'quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

For the purpose of QTL mapping, the markers included should be diagnostic of origin in order for inferences to be made about subsequent populations. SNP markers are ideal for mapping because the likelihood that a particular SNP allele is derived from independent origins in the extent populations of a particular species is very low. As such, SNP markers are useful for tracking and assisting introgression of QTLs, particularly in the case of haplotypes.

The genetic linkage of additional marker molecules can be established by a gene mapping model such as, without limitation, the flanking marker model reported by Lander et al., (Lander et al., 1989 Genetics, 121:185-199), and the interval mapping, based on maximum likelihood methods described therein, and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander et al., (1989), and further described by Arús and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak et al., 1995 Genetics, 139:1421-1428). Multiple regression methods or models can also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as "cofactors," have been reported by Jansen et al., (Jansen et al. 1994 Genetics, 136:1447-1455) and Zeng (Zeng 1994 Genetics 136:1457-1468). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng 1994). These models can be extended to multi-environment experiments to analyze genotype-environment interactions (Jansen et al., 1995 Theor. Appl. Genet. 91:33-3).

Selection of appropriate mapping populations is important to map construction. The choice of an appropriate mapping population depends on the type of marker systems employed (Tanksley et al., *Molecular mapping in plant chromosomes. chromosome structure and function: Impact of new concepts* J. P. Gustafson and R. Appels (eds.). Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

An $F_2$ population is the first generation of selfing. Usually a single $F_1$ plant is selfed to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938)). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., 1992 Proc. Natl. Acad. Sci. (USA) 89:1477-1481). However, as the distance between markers becomes larger (i.e., loci become more independent), the information in RIL populations decreases dramatically.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., 1992). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al. 1991 Proc. Natl. Acad. Sci. (U.S.A.) 88:9828-9832). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). A cultivar is a race or variety of a plant species that has been created or selected intentionally and maintained through cultivation.

Selected, non-limiting approaches for breeding the plants of the present invention are set forth below. A breeding program can be enhanced using marker assisted selection (MAS) on the progeny of any cross. It is understood that nucleic acid markers of the present invention can be used in a MAS (breeding) program. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred aspect, a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes.

Breeding lines can be tested and compared to appropriate standards in environments representative of the commercial target area(s) for two or more generations. The best lines are candidates for new commercial cultivars; those still deficient in traits may be used as parents to produce new populations for further selection.

The development of new elite corn hybrids requires the development and selection of elite inbred lines, the crossing of these lines and selection of superior hybrid crosses. The hybrid seed can be produced by manual crosses between selected male-fertile parents or by using male sterility systems. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (e.g., cultivar) and, in addition, the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of Crop Improvement," Longman, Inc., NY, 369-399, 1979; Sneep and Hendriksen, "Plant Breeding Perspectives," Wageningen (ed), Center for Agricultural Publishing and Documentation, 1979; Fehr, In: *Soybeans: Improvement, Production and Uses,* 2nd Edition, *Manograph.,* 16:249, 1987; Fehr, "Principles of Variety Development," *Theory and Technique*, (Vol. 1) and *Crop Species Soybean* (Vol. 2), Iowa State Univ., Macmillan Pub. Co., NY, 360-376, 1987).

An alternative to traditional QTL mapping involves achieving higher resolution by mapping haplotypes, versus individual markers (Fan et al., 2006 Genetics 172:663-686). This approach tracks blocks of DNA known as haplotypes, as defined by polymorphic markers, which are assumed to be identical by descent in the mapping population. This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are well within the skill of the ordinary practitioner of the art.

It is further understood, that the present invention provides bacterial, viral, microbial, insect, mammalian and plant cells comprising the nucleic acid molecules of the present invention.

As used herein, a "nucleic acid molecule," be it a naturally occurring molecule or otherwise may be "substantially purified", if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

The agents of the present invention may be labeled with reagents that facilitate detection of the agent (e.g. fluorescent labels (Prober et al., 1987 Science 238:336-340; Albarella et al., European Patent 144914), chemical labels (Sheldon et al., U.S. Pat. No. 4,582,789; Albarella et al., U.S. Pat. No. 4,563,417), modified bases (Miyoshi et al., European Patent 119448).

Having now generally described the invention, the same will be more readily understood through reference to the following examples which are provided by way of illustration, and are not intended to be limiting of the present invention, unless specified.

EXAMPLES

Having illustrated and described the principles of the present invention, it should be apparent to persons skilled in the art that the invention can be modified in arrangement and detail without departing from such principles. We claim all modifications that are within the spirit and scope of the appended claims.

Example 1: Inoculation and Phenotyping for Diplodia Ear Rot (DER)

Corn plant reaction to DER inoculation at various geographies was assessed and QTL and SNP markers associated with DER resistance were found by the following means. In order to assess reaction to DER, plants are artificially inoculated with either a mixture containing *Stenocarpella maydis* and *Stenocarpella macrospora* isolate or the isolates of either pathogen. Plants are inoculated by methods of deposition of a suspension of spores on the grain stalk, placing inoculum in the apical whorl of the plants according to Flett and McLaren (1994) and Bensch (1995) or inoculated according to Chambers (1988), Klapproth and Hawk (1991), and Villena (1969).

Resistance and susceptibility to DER can be determined by examination of ears or shelled grain.

Percentage of rotten ears is calculated after the ears are harvested at an average moisture of 18% to 21%. Ears are visually examined for symptoms of DER. Infected ears are expressed as a percentage of the total number of ears harvested in each plot.

Percentage of rotten grain is calculated after hand harvesting and shelling of the ears. Total grain weight and rotten grain weight are determined and percentage of rotten grain is used as phenotypic data. Herein, up to 8% rotten grain is considered resistant, 8-20% rotten grain is considered mid-resistant or tolerant, and greater than 20% rotten grain is considered susceptible.

Example 2: Mapping Population 2 (CV183/CV174+01HG14) for DER Using *Stenocarpella maydis*

DER is a widespread ear rot pathogen of corn which is presented in many countries. To identify QTL and SNP markers associated with DER resistance, reaction of inoculated corn plants was assessed in Argentina, USA, and South Africa. In the present invention QTL and SNP markers associated with DER resistance were identified by the following means. A mapping population was developed for identifying corn genomic regions associated with DER. A mapping population of 146 individuals from $F_{2:3}$ families was developed from the CV183/CV174 population. Trials were conducted across three geographies. Trials were evaluated at three locations in Argentina (1 replication per location), two locations in the USA (2 replications per location), and at four locations in South Africa (2 replications per location). Plants were artificially inoculated with *Stenocarpella maydis*, and DER incidence data were collected. Phenotypic DER incidence was calculated as percentage of infected ears within a plot. Genomic DNA was isolated from the $F_{2:3}$ families and screened with 123 SNP markers. After quality control analysis, 115 markers were chosen for the mapping study. QTL mapping was performed with Windows QTL Cartographer Version 2.5 using Composite Interval Mapping (CIM) with a forward regression method. Multiple Interval Mapping (MIM) was used to further refine the QTL mapping using a forward regression selection method on markers. Criteria for the model selection were set at a probability of partial $R^2$ at a significance level of 0.01. MIM was performed for each geography, pairwise combination, combinations of the geographies, and combined across all geographies by estimating the QTL effects, optimizing the QTL positions, and searching for new QTLs via Main QTLs and QTL interactions. FIG. 1 provides the QTL with flanking SNP markers found to be associated with DER. The QTL and SNP markers provided in the present invention can be used to introgress resistance to DER into corn plants.

Example 3: Mapping Population 3 (CV128/CV162) for DER Using a Mixture of *Stenocarpella macrospora* and *Stenocarpella maydis*

DER is a widespread ear rot pathogen of corn which is presented in many countries. To identify QTL and SNP markers associated with DER resistance, reaction of inoculated corn plants was assessed in central Brazil. Of the two DER pathogens in Brazil, *S. macrospora* is more prominent in the central region and *S. maydis* is more prominent in the south. In the present invention, QTL and SNP markers associated with DER resistance were identified by the following means. A mapping population was developed for identifying corn genomic regions associated with DER resistance. In the mapping population, 769 $F_2$ progenies were developed from the cross CV128/CV162. The field trial was conducted in central Brazil in a complete randomized block design with three replications. Plants were artificially inoculated twice with a mixture of *Stenocarpella macrospora* and *Stenocarpella maydis* by deposition of fungal spores at the insertion of the shank with the stalk. Phenotypic DER incidence was calculated as percentage of rotten grain from total grain. Genomic DNA was screened with 117 SNP markers. Single marker analysis was performed by simple linear regression. A multiple regression model with all significant markers was performed, and the model was further refined with a stepwise procedure with a 0.15 significance level for one marker entry and 0.10 significance level to remain in the model. FIG. 2 provides QTL and SNP markers associated with DER resistance from this mapping study.

Example 4: Mapping Population (CV128*2/CV162) for DER Using *Stenocarpella macrospora* and *Stenocarpella maydis*

DER is a widespread ear rot pathogen of corn which is presented in many countries. To identify QTL and SNP markers associated with DER resistance, reaction of inoculated corn plants was assessed in Central Brazil. In the present invention, QTL and SNP markers associated with DER resistance were validated by the following means. A population of 260 BC1F3 individuals was developed from the cross CV128*2/CV162. The study was conducted in central Brazil in a complete randomized block design with four replications. Two replications were artificially inoculated with *Stenocarpella maydis*, and two were artificially inoculated with *Stenocarpella macrospora*. Three inoculations were made by deposition of fungal spores at the insertion of the shank with the stalk. Phenotypic DER incidence was calculated as percentage of rotten grain from total grain. Genomic DNA was screened with a total of 170 SNP markers. QTL and SNP markers found to be associated with DER resistance from *Stenocarpella macrospora* are provided in FIG. 3. QTL and SNP markers found to be associated with DER resistance from *Stenocarpella maydis* are provided in FIG. 4. QTL associated with resistance to DER from *S. macrospora* were identified on Chromosomes 4 and 7. On Chromosome 4, a QTL was identified that was associated with resistance to DER from *S. maydis*.

Example 5: Mapping Population (CV162/CV129+CV128) Using *Stenocarpella maydis* and *Stenocarpella macrospora* in Central Brazil DER is a widespread ear rot pathogen of corn which is presented in many countries. To identify QTL and SNP markers associated with DER resistance, reaction of inoculated corn plants was assessed in Central Brazil. In the present invention, QTL and SNP markers associated with DER resistance were identified by the following means. A mapping population was developed for identifying corn genomic regions associated with DER resistance. In the mapping population, 140 doubled haploids (DH) progenies were developed from crossing two inbred lines, CV162 and CV129.

Each DH progeny was test-crossed to the susceptible tester CV128 and the resulting hybrids were evaluated at three different locations within the Central region of Brazil with two replications per site, during the summer season of 2005-2006. After flowering time, all ears were artificially inoculated with a mixture of *Stenocarpella maydis*, *Stenocarpella macrospora* and *Fusarium moniliforme*. This mixture has been widely used by the breeding program in Brazil to screen for a disease complex known as Grãos Ardidos. Harvest of yield trials was performed by hand and phenotypic DER incidence was calculated as percentage of rotten ears.

Genomic DNA was isolated from every DH progeny and screened with 106 SNP markers. QTL mapping was performed with QTL cartographer Version 2.5 from North Caroline State University, using Composite interval mapping (CIM) with a forward regression method and cross type set to Ri0 (Recombinant inbred line, derived by doubled haploid lines). Data for this Example is shown in FIG. 5.

Regions on chromosomes three and five exhibited consistency across locations and years when compared with the results given in Example 6.

Example 6: DER Mapping Population (CV162/CV129+CV128) Using *Stenocarpella maydis* and *Stenocarpella macrospora* in Central and Southern Brazil DER is a widespread ear rot pathogen of corn which is presented in many countries. To identify QTL and SNP markers associated with DER resistance, reaction of inoculated corn plants was assessed in Central and Southern Brazil. In the present invention, QTL and SNP markers associated with DER resistance were identified by the following means. A mapping population was developed for identifying corn genomic regions associated with DER resistance. In the mapping population, 144 doubled haploids (DH) progenies were developed from crossing two inbred lines, CV162 and CV129. During 2006-2007, plants were grown in southern and central Brazil at three different locations in each geography. Plants were artificially inoculated with a mixture of *Stenocarpella maydis* and *Stenocarpella macrospora* by depositing a suspension of spores on the plant. Genomic DNA was screened with 107 SNP markers. Percentage of rotten ears was used as phenotypic data in the mapping analysis. FIG. 6 provides QTL and flanking SNP markers associated with DER resistance. The QTL and SNP markers provided can be used for introgressing DER resistance into corn plants.

Example 7: Exemplary Marker Assays for Detecting DER Resistance

In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means. Exemplary primers and probes for amplifying and detecting genomic regions associated with DER resistance are given in Table 1.

TABLE 1

Exemplary assays for detecting DER resistance.

| Marker | Marker SEQ ID | SNP Position | SEQ ID Forward Primer | SEQ ID Reverse Primer | SEQ ID Probe 1 | SEQ ID Probe 2 |
|---|---|---|---|---|---|---|
| NC0003210 | 27 | 129 | 48 | 49 | 56 | 57 |
| NC0106527 | 28 | 356 | 50 | 51 | 58 | 59 |
| NC0015344 | 5 | 420 | 52 | 53 | 60 | 61 |
| NC0016137 | 6 | 482 | 54 | 55 | 62 | 63 |

Example 8: Oligonucleotide Hybridization Probes Useful for Detecting Corn Plants with DER Resistance Loci Oligonucleotides can also be used to detect or type the polymorphisms associated with DER resistance disclosed herein by hybridization-based SNP detection methods. Oligonucleotides capable of hybridizing to isolated nucleic acid sequences which include the polymorphism are provided. It is within the skill of the art to design assays with experimentally determined stringency to discriminate between the allelic states of the polymorphisms presented herein. Exemplary assays include Southern blots, Northern blots, microarrays, in situ hybridization, and other methods of polymorphism detection based on hybridization. Exemplary oligonucleotides for use in hybridization-based SNP detection are provided in Table 2. These oligonucleotides can be detectably labeled with radioactive labels, fluorophores, or other chemiluminescent means to facilitate detection of hybridization to samples of genomic or amplified nucleic acids derived from one or more corn plants using methods known in the art.

TABLE 2

Oligonucleotide Hybridization Probes

| Marker | Marker SEQ ID | SNP Position | Hybridization Probe | SEQ ID Probe |
|---|---|---|---|---|
| NC0003210 | 27 | 129 | TTTTTGTCTCAAAGTA | 64 |
| NC0003210 | 27 | 129 | TTTTTGTGTCAAAGTA | 65 |
| NC0106527 | 28 | 356 | ACCATACGGACCCACT | 66 |
| NC0106527 | 28 | 356 | ACCATACCGACCCACT | 67 |
| NC0015344 | 5 | 420 | GGAGGCAGTTCTTTTG | 68 |
| NC0015344 | 5 | 420 | GGAGGCAATTCTTTTG | 69 |
| NC0016137 | 6 | 482 | TGGGTGCTACTGCTTC | 70 |
| NC0016137 | 6 | 482 | TGGGTGCCACTGCTTC | 71 |

*SNPs in bold print and underlined

Example 9: Oligonucleotide Probes Useful for Detecting Corn Plants with DER Resistance Loci by Single Base Extension Methods Oligonucleotides can also be used to detect or type the polymorphisms associated with DER resistance disclosed herein by single base extension (SBE)-based SNP detection methods. Exemplary oligonucleotides for use in SBE-based SNP detection are provided in Table 9. SBE methods are based on extension of a nucleotide primer that is hybridized to sequences adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type polymorphisms disclosed in this invention are provided in Table 3 in the columns labeled "Forward Primer SEQ ID" and "Reverse Primer SEQ ID". Following amplification of the region containing the polymorphism, the PCR product is hybridized with an extension primer which anneals to the amplified DNA adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

TABLE 3

Probes (extension primers) for Single Base Extension (SBE) assays.

| Marker | Marker SEQ ID | SNP Position | Probe (SBE) | Probe SEQ ID |
|---|---|---|---|---|
| NC0003210 | 27 | 129 | TAAAACCTTT TTTTGTC | 72 |
| NC0003210 | 27 | 129 | CTGAGGCAAT ACTTTGA | 73 |
| NC0106527 | 28 | 356 | TGGCAACAAA CCATACG | 74 |
| NC0106527 | 28 | 356 | TGAAGAATAA GTGGGTC | 75 |
| NC0015344 | 5 | 420 | AAAATGTTGG GAGGCAG | 76 |
| NC0015344 | 5 | 420 | AATGGGCAGC AAAAGAA | 77 |
| NC0016137 | 6 | 482 | CCAGCTGCGT GGGTGCT | 78 |
| NC0016137 | 6 | 482 | TCTCTATCAG AAGCAGT | 79 |

Example 10: Introgress Ion of DER Resistance into a Corn Plant

Corn breeders can use the SNP markers provided in the present invention to introgress DER resistance into a corn plant. The markers provided in Table 4 can be used to monitor the introgression of DER resistance QTL into a corn plant. In addition, Table 4 includes exemplary sources of DER resistance.

The introgression of one or more resistance loci is achieved via one or more cycles of backcrossing to a recurrent parent with one or more preferred agronomic characteristics, accompanied by selection to retain the one or more DER resistance loci from the donor parent using the markers of the present invention. Introgression can be monitored by genotyping one or more plants and determining the allelic state of the one or more DER resistance loci. This backcross procedure is implemented at any stage in variety development and occurs in conjunction with breeding for one or more traits of interest including transgenic and nontransgenic traits.

Alternatively, a forward breeding approach is employed wherein one or more DER resistance loci can be monitored for successful introgression following a cross with a susceptible parent with subsequent generations genotyped for one or more DER resistance loci and for one or more additional traits of interest, including transgenic and nontransgenic traits.

TABLE 4

Summary of SNP markers associated with DER resistance and exemplary sources of DER resistance for each allele.

| Marker | Chrom | Pos | DER res. Locus | SEQ ID marker | Res. Allele | Susc. Allele | Resistant Source | SNP Position |
|---|---|---|---|---|---|---|---|---|
| NC0009449 | 1 | 82.0 | 1 | 1 | AA | GG | CV174 | 188 |
| NC0025863 | 1 | 96.7 | 1 | 2 | AA | GG | CV174 | 129 |
| NC0199970 | 1 | 191.6 | 2 | 3 | TT | CC | CV129 | 386 |
| NC0039486 | 1 | 207.9 | 2 | 4 | AA | CC | CV129 | 206 |
| NC0015344 | 1 | 221.1 | 3 | 5 | GG | AA | CV162 | 420 |
| NC0016137 | 1 | 256.3 | 3 | 6 | CC | TT | CV162 | 482 |
| NC0106389 | 3 | 14.2 | 4 | 7 | GG | AA | CV162 | 222 |
| NC0199309 | 3 | 83.2 | 5 | 8 | AA | GG | CV162 | 303 |
| NC0009470 | 3 | 88.0 | 4 | 9 | GG | CC | CV162 | 137 |
| NC0199941 | 3 | 99.2 | 5 | 10 | AA | GG | CV162 | 101 |
| NC0030587 | 3 | 179.7 | 6 | 11 | AA | CC | CV183 | 84 |
| NC0019414 | 3 | 204.2 | 6 | 12 | AA | CC | CV183 | 275 |
| NC0009057 | 4 | 21.7 | 7 | 13 | TT | GG | CV162 | 229 |
| NC0199875 | 4 | 46.8 | 7 | 14 | TT | GG | CV162 | 125 |
| NCO201962 | 4 | 71.0 | 8 | 15 | TT | GG | CV162 | 244 |
| NC0105550 | 4 | 94.8 | 8 | 16 | ************ | CCTACCTTCAGAA | CV162 | 241-253 |
| NC0032557 | 4 | 95.1 | 9 | 17 | CC | GG | CV174 | 413 |
| NC0105197 | 4 | 99.9 | 10 | 18 | CC | TT | CV129 | 321 |
| NC0009620 | 4 | 109.2 | 9 | 19 | TT | GG | CV174 | 175 |
| NCO200096 | 4 | 120.8 | 10 | 20 | GG | TT | CV129 | 165 |
| NC0009668 | 5 | 65.2 | 11 | 21 | GG | AA | CV129 | 1 |
| NC0111346 | 5 | 79.0 | 12 | 22 | AA | CC | CV162 | 366 |
| NCO200395 | 5 | 81.3 | 11 | 23 | GG | CC | CV129 | 163 |
| NC0040366 | 5 | 84.1 | 12 | 24 | AA | CC | CV162 | 119 |
| NCO202210 | 5 | 107.8 | 13 | 25 | TT | CC | CV129 | 321 |
| NCO200106 | 5 | 124.2 | 13 | 26 | CC | TT | CV129 | 241 |
| NC0003210 | 6 | 38.4 | 14 | 27 | CC | GG | CV183 | 129 |
| NC0106527 | 6 | 56.4 | 14 | 28 | CC | GG | CV183 | 356 |
| NC0008833 | 6 | 70.9 | 15 | 29 | CC | AA | CV162 | 179 |
| NC0004030 | 6 | 85.5 | 16 | 30 | GG | AA | CV162 | 312 |
| NCO201579 | 6 | 88.0 | 15 | 31 | AA | GG | CV162 | 91 |
| NC0088767 | 6 | 99.0 | 16 | 32 | CC | AA | CV162 | 536 |
| NCO202487 | 6 | 103.0 | 17 | 33 | CC | AA | CV162 | 377 |
| NC0199561 | 6 | 118.1 | 17 | 34 | TT | AA | CV162 | 728 |
| NCO201942 | 7 | 34.5 | 18 | 35 | CC | TT | CV129 | 271 |
| NC0013158 | 7 | 48.6 | 19 | 36 | GG | TT | CV162 | 382 |

TABLE 4-continued

Summary of SNP markers associated with DER resistance and exemplary sources of DER resistance for each allele.

| Marker | Chrom | Pos | DER res. Locus | SEQ ID marker | Res. Allele | Susc. Allele | Resistant Source | SNP Position |
|---|---|---|---|---|---|---|---|---|
| NC0009409 | 7 | 51.2 | 18 | 37 | CC | TT | CV129 | 294 |
| NC0040322 | 7 | 64.5 | 20 | 38 | AA | CC | CV162 | 41 |
| NC0029362 | 7 | 78.4 | 19 | 39 | TT | CC | CV162 | 106 |
| NC0029362 | 7 | 78.4 | 20 | 39 | TT | CC | CV162 | 106 |
| NC0082612 | 8 | 78.9 | 21 | 40 | AA | GG | CV174 | 309 |
| NC0013946 | 8 | 84.0 | 21 | 41 | GG | AA | CV174 | 59 |
| NCO200572 | 8 | 95.6 | 22 | 42 | GG | TT | CV162 | 270 |
| NC0031630 | 8 | 125.1 | 22 | 43 | CC | TT | CV162 | 645 |
| NC0104512 | 10 | 57.3 | 23 | 44 | TT | AA | CV129 | 79 |
| NCO201713 | 10 | 71.7 | 23 | 45 | CC | TT | CV129 | 145 |
| NC0009486 | 10 | 105.5 | 24 | 46 | TT | AA | CV183 | 166 |
| NC0008643 | 10 | 119.1 | 24 | 47 | GG | AA | CV183 | 241 |

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

Various patent and non-patent publications are cited herein, the disclosures of each of which are, to the extent necessary, incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

What is claimed is:

1. A method of identifying a corn plant comprising at least one allele associated with diplodia ear rot resistance or with diplodia ear rot tolerance in a corn plant, the method comprising:
   (a) genotyping a population of corn plants with at least one corn genomic nucleic acid marker associated with an allele for diplodia ear rot resistance or diplodia ear rot tolerance, wherein said allele comprises a marker selected from the group consisting of SEQ ID NO: 21 and SEQ ID NO: 23;
   (b) selecting based upon said genotyping at least one corn plant comprising the allele associated with resistance or tolerance to diplodia ear rot; and
   (c) crossing the corn plant selected in step (b) to another corn plant.

2. The method according to claim 1, wherein the population of corn plants genotyped in step (a) and/or the at least one corn plant selected in step (b) is a corn plant from a population generated by a cross.

3. The method according to claim 1, wherein said genotyping in step (a) is with at least the corn genomic nucleic acid marker of SEQ ID NO: 21.

4. The method according to claim 1, wherein said genotyping in step (a) is with at least the corn genomic nucleic acid marker of SEQ ID NO: 23.

5. The method according to claim 1, wherein the selected one or more corn plants exhibit at least tolerance to a diplodia ear rot-inducing fungus or exhibit at least resistance to a diplodia ear rot-inducing fungus.

6. The method according to claim 2, wherein said population is generated by a cross of at least one diplodia ear rot resistant corn plant with at least one diplodia ear rot sensitive corn plant.

7. The method according to claim 1, further comprising the step (d) of assaying the selected corn plant for resistance to a diplodia ear rot-inducing fungus.

8. The method of claim 1, further comprising the step of obtaining seed from the corn plant selected in step (b).

9. The method of claim 1, wherein resistance or tolerance is to a diplodia ear rot-inducing fungus selected from the group consisting of *Stenocarpella maydis* and *Stenocarpella macrospora*.

* * * * *